United States Patent
Brugger et al.

(10) Patent No.: US 7,419,597 B2
(45) Date of Patent: Sep. 2, 2008

(54) FLUID, CIRCUITS, SYSTEMS, AND PROCESSES FOR EXTRACORPOREAL BLOOD PROCESSING

(75) Inventors: James M. Brugger, Newburyport, MA (US); Jeffrey H. Burbank, Boxford, MA (US); Dennis M. Treu, Bedford, NH (US)

(73) Assignee: Nxstage Medical Inc., Lawrence, MA (US)

( * ) Notice: Subject to any disclaimer, the term of this patent is extended or adjusted under 35 U.S.C. 154(b) by 0 days.

(21) Appl. No.: 11/695,739

(22) Filed: Apr. 3, 2007

(65) Prior Publication Data

US 2007/0185430 A1 Aug. 9, 2007

Related U.S. Application Data

(60) Division of application No. 10/650,935, filed on Aug. 27, 2003, now Pat. No. 7,214,312, which is a continuation-in-part of application No. 09/905,246, filed on Jul. 12, 2001, now Pat. No. 6,649,063.

(51) Int. Cl.
 *B01D 61/24* (2006.01)
 *B01D 61/26* (2006.01)
 *B01D 61/30* (2006.01)

(52) U.S. Cl. ............... 210/646; 210/645; 210/650; 210/798; 210/805; 604/5.04; 604/6.09; 604/6.11

(58) Field of Classification Search ............... 210/644, 210/645, 646, 650, 793, 798, 805, 180, 188, 210/194, 195.1, 195.2, 257.1, 257.2, 258, 210/321.6, 321.69, 321.71, 416.1, 436, 472; 604/5.04, 6.09, 6.11

See application file for complete search history.

(56) References Cited

U.S. PATENT DOCUMENTS

| | | | |
|---|---|---|---|
| 2,409,343 A | | 10/1946 | Curtis |
| 3,485,245 A | * | 12/1969 | Terwilliger et al. ......... 604/114 |
| 3,840,458 A | * | 10/1974 | Deinger et al. .............. 424/582 |
| D285,079 S | | 8/1986 | Huthmacher |
| 4,629,448 A | | 12/1986 | Carlsson et al. |
| 4,698,153 A | | 10/1987 | Matsuzaki et al. |
| 4,796,696 A | * | 1/1989 | Stocton et al. .............. 165/169 |
| 4,825,168 A | | 4/1989 | Ogawa et al. |
| 4,851,866 A | | 7/1989 | Ciarlei et al. |
| 4,976,685 A | | 12/1990 | Block, Jr. |
| 5,090,774 A | | 2/1992 | Dolla |
| 5,476,592 A | | 12/1995 | Simard |
| 5,616,305 A | | 4/1997 | Mathieu |
| 5,650,071 A | | 7/1997 | Brugger et al. |
| 5,679,245 A | | 10/1997 | Manica |
| 5,687,764 A | | 11/1997 | Tanaka et al. |
| 5,698,090 A | | 12/1997 | Bene et al. |
| 5,702,597 A | | 12/1997 | Chevallet et al. |

(Continued)

FOREIGN PATENT DOCUMENTS

WO          WO 98/16269          *   4/1998

*Primary Examiner*—John Kim
(74) *Attorney, Agent, or Firm*—Miles & Stockbridge P.C.; Mark A. Catan

(57) ABSTRACT

A method for renal replacement therapy includes priming a fluid circuit and recirculating the sterile fluid during priming to permit gas to float out of the sterile fluid into a fluid reservoir. The fluid is preferably either warmed during circulation or vibrated to promote the removal of gas.

16 Claims, 23 Drawing Sheets

U.S. PATENT DOCUMENTS

| | | |
|---|---|---|
| 5,725,776 A | 3/1998 | Kenley et al. |
| 5,744,027 A | 4/1998 | Connell et al. |
| 5,762,805 A | 6/1998 | Truitt et al. |
| 5,776,345 A * | 7/1998 | Truitt et al. .................. 210/645 |
| 5,808,181 A * | 9/1998 | Wamsiedler et al. ........... 73/38 |
| 5,846,419 A | 12/1998 | Nederlof |
| 5,863,421 A | 1/1999 | Peter, Jr. et al. |
| 5,871,694 A | 2/1999 | Beden et al. |
| 5,895,368 A | 4/1999 | Utterberg |
| 5,919,154 A | 7/1999 | Toavs et al. |
| 5,951,870 A | 9/1999 | Utterberg |
| 6,039,877 A | 3/2000 | Chevallet et al. |
| 6,042,784 A | 3/2000 | Wamsiedler et al. |
| 6,044,691 A | 4/2000 | Kenley et al. |
| 6,066,261 A | 5/2000 | Spickermann |
| 6,132,616 A * | 10/2000 | Twardowski et al. ........ 210/646 |
| 6,136,201 A * | 10/2000 | Shah et al. .................. 210/739 |
| 6,146,536 A | 11/2000 | Twardowski |
| 6,187,198 B1 | 2/2001 | Utterberg |
| 6,187,207 B1 * | 2/2001 | Brauer ....................... 210/739 |
| 6,280,632 B1 * | 8/2001 | Polaschegg ................. 210/739 |
| 6,290,665 B1 | 9/2001 | Utterberg |
| 6,344,139 B1 | 2/2002 | Utterberg et al. |
| 6,387,069 B1 | 5/2002 | Utterberg |
| 6,464,878 B2 | 10/2002 | Utterberg |
| 6,551,276 B1 * | 4/2003 | Mann et al. .................. 604/131 |
| 6,582,385 B2 * | 6/2003 | Burbank et al. ............ 604/5.04 |
| 6,881,211 B2 | 4/2005 | Schweikert et al. |
| 6,979,309 B2 | 12/2005 | Burbank et al. |
| 7,166,084 B2 | 1/2007 | Utterberg |
| 2004/0054321 A1 | 3/2004 | Schon et al. |
| 2004/0122418 A1 | 6/2004 | Voorhees |
| 2005/0011833 A1 | 1/2005 | Stahl |
| 2005/0020958 A1 | 1/2005 | Paolini et al. |
| 2005/0045540 A1 | 3/2005 | Connell et al. |
| 2005/0061740 A1 | 3/2005 | Felding et al. |
| 2005/0065459 A1 | 3/2005 | Zhang et al. |
| 2005/0082210 A1 | 4/2005 | Favre |
| 2005/0115070 A1 | 6/2005 | Sugimoto et al. |
| 2005/0126998 A1 | 6/2005 | Childers |
| 2005/0131331 A1 | 6/2005 | Kelly et al. |
| 2005/0131332 A1 | 6/2005 | Kelly et al. |
| 2005/0171469 A1 | 8/2005 | Cunningham |
| 2005/0171501 A1 | 8/2005 | Kelly |
| 2005/0197612 A1 | 9/2005 | Levin et al. |
| 2005/0209547 A1 * | 9/2005 | Burbank et al. ............ 604/5.01 |
| 2005/0251086 A1 | 11/2005 | Sternby |
| 2005/0288623 A1 | 12/2005 | Hjalmarsson |
| 2007/0106196 A1 | 5/2007 | Utterberg |

* cited by examiner

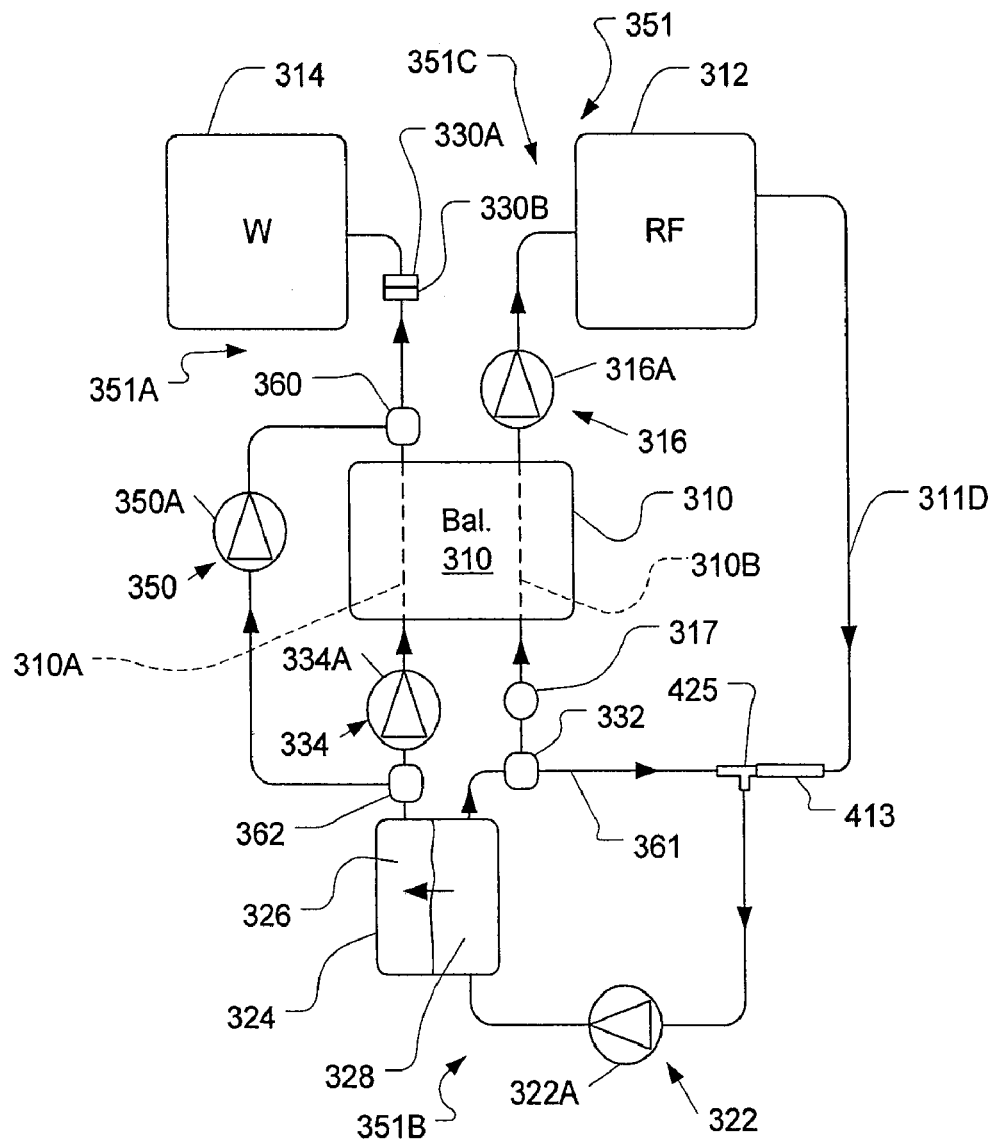
*Fig. 11D*
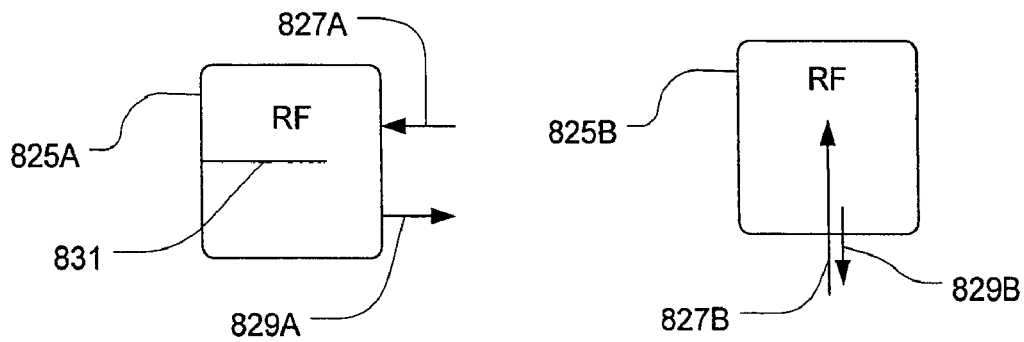
*Fig. 11E*          *Fig. 11F*

US 7,419,597 B2

FLUID, CIRCUITS, SYSTEMS, AND PROCESSES FOR EXTRACORPOREAL BLOOD PROCESSING

REFERENCE TO RELATED APPLICATIONS

This is a divisional application Ser. No. 10/650,935, filed Aug. 27, 2003, now U.S. Pat. No. 7,214,312, which is a continuation-in-part of Ser. No. 09/905,246, filed Jul. 12, 2001, now U.S. Pat. No. 6,649,063, the entireties of which are hereby incorporated by reference.

FIELD OF THE INVENTION

The present invention relates generally to medical devices and methods for renal replacement therapy and also to various safety features, particularly related to ensuring a low rate of pyrogenic material in infusible fluids.

BACKGROUND OF THE INVENTION

Patients undergoing hemofiltration, hemodialysis, hemodiafiltration, ultrafiltration, or other form of renal replacement therapy need replacement fluid, dialysate, or infusate which is free of biological contaminants. Given the large amount of purified fluid needed by such therapies and the current method of spiking multiple bags of replacement fluid, dialysate, or infusate, there is a risk of touch contamination resulting in the introduction of biological contaminants into the fluids. Making the appropriate connections, then filtering the fluid greatly reduces this risk to the patient. It would be advantageous if the same equipment used in renal replacement therapy, such as hemofiltration, could be reconfigured for on-line decontamination of prepackaged solutions such as dialysate to produce the large volumes of purified replacement fluid required for the therapy.

Presently methods to produce volumes of dialysate from tap water are known, but require complex water purification/ standardization equipment, since impurities and cleaning additives such as chlorine vary greatly in tap water from municipality to municipality and within a municipality over time. (See Twardowski U.S. Pat. Nos. 6,146,536 and 6,132,616.)

Moreover, dialysate solution, whether prepared online or prepackaged, while of the proper concentration for use as a purified replacement fluid, is not deemed to be sufficiently free of pathogenic contaminants to allow the injection of such a fluid into a patient. In hemodialysis, the dialysate never enters the patient's body, but instead flows past a semipermeable membrane that permits impurities in the blood to osmose through the membrane from the higher concentration blood to the lower concentration dialysate. Thus dialysate, intended for extracorporeal use only, is less expensive than solutions prepared as replacement fluids, which will be injected into a patient.

Attempts to render dialysate sufficiently purified for use as a replacement fluid in hemofiltration and hemodiafiltration have focused on a continuous sterilization process that requires a separate dialysate filtration/purification apparatus that must be periodically purged and verified to provide sufficient constant flow of purified replacement fluid required for hemofiltration. (See Chavallet U.S. Pat. Nos. 6,039,877 and 5,702,597.) Such devices are necessarily complicated and require separate pumping systems for the sterilization process.

At least one prior art reference U.S. Pat. No. 6,280,632B1 shows purified replacement fluid being created during dialysis treatment by filtering the dialysate online. However, the technique shown requires a filter for this purpose. Since it is desirable, for safety reasons to make as much of the purified part of the fluid circuit used in blood treatment disposable and since filters are expensive, the need for an additional filter is a cost concern.

SUMMARY OF THE INVENTION

The present invention provides devices and methods for producing purified replacement fluid in a unit that is subsequently used for renal replacement therapy on a patient. The system can be used both to purify non-purified fluid and to further purify sterile fluid contaminated (e.g., by touch contamination) during connection due to improper technique. In a first embodiment, a system is provided to perform a method that includes the steps of providing a renal replacement therapy unit that has a filter with a membrane separating a waste side of the filter from a clean side. The membrane has a pore size smaller than the non-purified and pyrogenic material to be filtered. The renal replacement therapy unit also includes a first container of a solution of suitable concentration for use as a replacement fluid that may include the pyrogenic material or otherwise sterile fluid which has been contaminated (e.g., by touch contamination) during connection due to improper technique. The first container is in fluid communication with the waste side of the filter. The unit also includes a second container that is adapted to hold purified replacement fluid. The second container is in fluid communication with the clean side of the filter. A pump, generally the ultrafiltrate pump, is in fluid communication with the first container and the second container. The pump is capable of switching between a first direction that pumps fluid out of the first container and a second direction that removes waste from blood. A second pump, called a replacement fluid pump, pumps fluid out of the second container. The method further includes the step of running the pump in the first (reverse) direction to pump the solution of suitable concentration from the first container into the waste side of the filter. The solution from the first container is filtered through the membrane of the filter to trap the pyrogenic material on the waste side of the filter and produce purified replacement fluid in the clean side of the filter. The purified replacement fluid that flows from the clean side of the filter is collected in the second container. During therapy the pump switches to run in the second (forward) direction to pump waste from the blood. The purified replacement fluid is pumped from the second container into the blood by a second pump. The purified replacement fluid is used to perform renal replacement therapy on a patient.

Another embodiment is a pre-connected, purified fluid management kit for use in presterilizing replacement fluids prior to renal replacement therapy. The kit includes various disposable components of a renal replacement therapy unit. In one embodiment, the kit includes a fluid pumping and balancing system, a purified fluid reservoir, a plurality of tubes conventionally used in a renal replacement therapy, and a replacement fluid container. Each of the plurality of tubes has a first end in fluid communication with the fluid pumping and balancing system and a second end releasably coupled to and in fluid communication with the purified fluid reservoir. The replacement fluid container tube has a first end coupled to the fluid pumping and balancing system and a second end adapted to couple to a replacement fluid container. The kit is sterilized and packaged in a container at the time of manufacturing to prevent contamination prior to use in a renal replacement therapy unit.

Another embodiment is a system for batch sterilization of replacement fluid and renal replacement therapy using the purified fluid. The system includes a renal replacement therapy unit adapted to releasably receive a sterilized kit and a sterilized kit having preconnected disposable elements of the renal replacement therapy unit. The kit includes a fluid pumping and balancing system, a plurality of connectors, each having a first end coupled to the fluid pumping and balancing system and a second end adapted to releasably couple to the renal replacement therapy unit, a purified replacement fluid container releasably coupled to the fluid pumping and balancing system through a plurality of tubes, and a tube having a first end coupled to the fluid pumping and balancing system and a second end adapted to releasably couple to a container of solution to be purified.

Another embodiment is a method for producing purified replacement fluid in a renal replacement therapy unit. The method includes the steps of providing a renal replacement therapy unit, a sterilized kit that includes certain disposable elements of the unit, and a container of solution of suitable concentration for use as a replacement fluid. The unit is adapted to releasably receive the sterilized kit. The kit includes a plurality of tubes adapted to releasably couple to the renal replacement therapy unit, a preconnected purified replacement fluid container and a tube having an end adapted to releasably couple to the solution container. The method further includes the steps of releasably coupling the sterilized kit to the renal replacement therapy unit, releasably coupling the tube to the container of a solution of suitable concentration for use as a replacement fluid, pumping the solution through the renal replacement therapy unit to sterilize it, and capturing the purified solution in the purified replacement fluid container for use in renal replacement therapy.

Another embodiment includes a purified disposable fluid circuit with no connections that are exposed for contamination. Replacement fluid can be generated using the fluid circuit in a manner that safeguards against touch contamination. The embodiment may use a double lumen access spike that is permanently bonded to the fluid circuit as described in U.S. patent application Ser. No. 10/393,209, for "Blood Circuit with Leak-Safe Features" and filed Mar. 20, 2003, hereby incorporated by reference as if fully set forth in its entirety herein. An automatically sealing connector may be provided to allow the access needle to be used for filtering replacement fluid, priming, and treatment.

Another embodiment demonstrates how filtering of replacement fluid by using the same filter as used for dialysis allows the saving of a filter while still ensuring against contamination risk.

According to an embodiment, a method is disclosed for performing renal replacement therapy with a treatment device that employs a fluid circuit with liquid and blood fluid circuits separated by a membrane, the membrane having a pore size effective to block the passage of pyrogenic material. The method comprises: connecting a source of electrolytically-balanced fluid to the liquid fluid circuit; ensuring sterility of the electrolytically-balanced fluid by passing the same through the membrane to produce sterile fluid and storing the sterile fluid in a reservoir; warming and maintaining a temperature of the sterile fluid until a treatment time; recirculating the sterile fluid through the reservoir to permit gas to be purged from the sterile fluid and prime a first portion of the fluid circuit; priming a further portion of the fluid circuit.

In a variation, the priming a further portion is executed after the recirculating. The methods may include conveying blood from a patient through the blood fluid circuit during a treatment cycle and removing waste from the blood from the blood circuit through the membrane to the liquid fluid circuit. The method may further include using the sterile fluid from reservoir in the process of performing a blood waste removing process on a patient. The methods may further include ensuring sterility includes ensuring a rate of endotoxins below a predetermined level by filtering with a membrane with a pore size effective to limit endotoxins. The predetermined level may be 3 EUs/ml. or less. The methods may further include vibrating the reservoir to aid in the removal of gas.

BRIEF DESCRIPTION OF THE DRAWINGS

FIG. 11D illustrates the use of the embodiment of FIG. 11B with a fluid circuit during priming.

FIGS. 11E and 11F illustrate mechanisms for ensuring that bubbles are given an opportunity to settle out of a priming flow.

DETAILED DESCRIPTION

Figure 1:
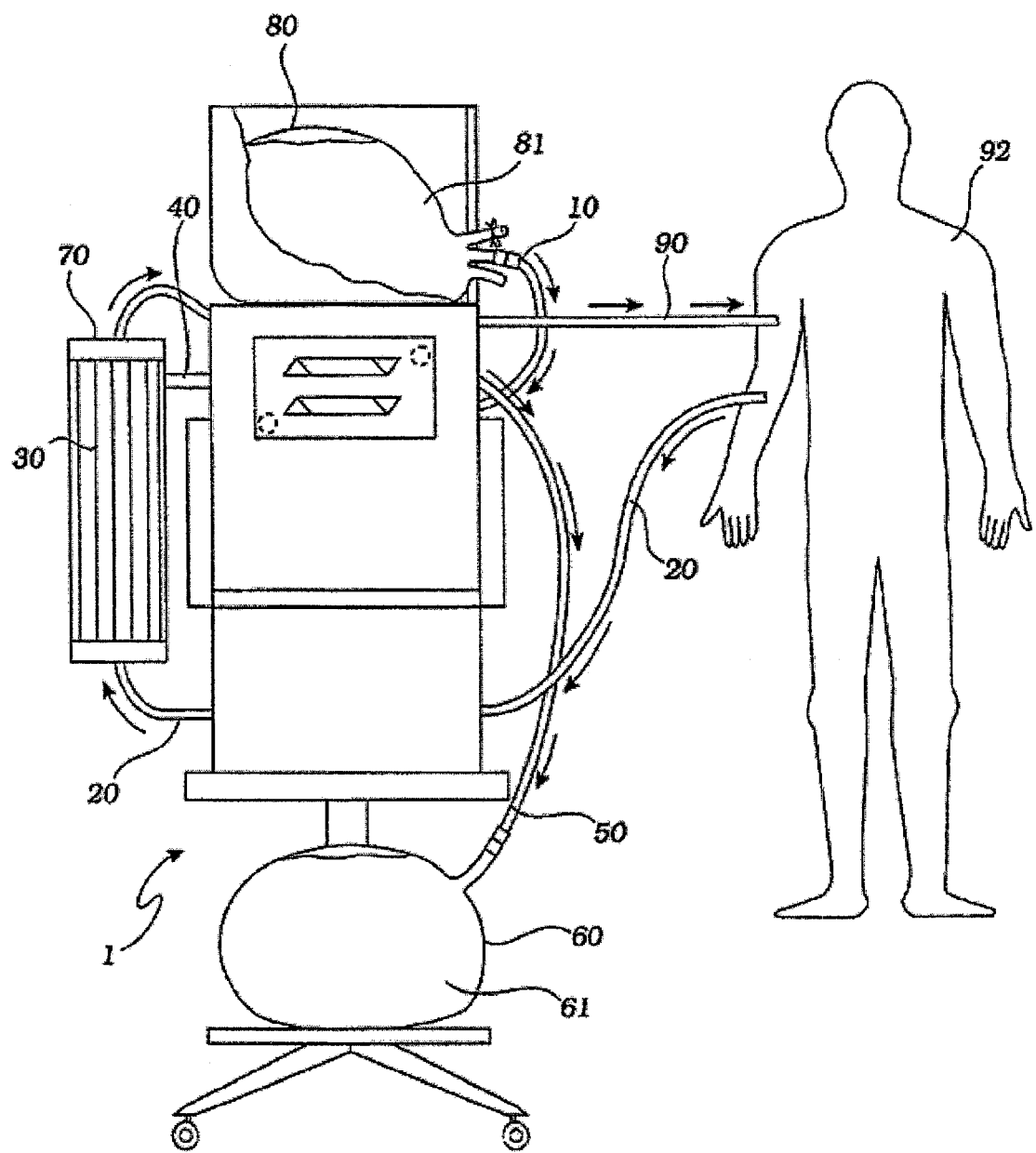
FIG. 1 depicts an embodiment of a hemofiltration unit performing the therapy.

A hemofiltration device 1 is depicted in FIG. 1. In a conventional forward pumping hemofiltration mode, a draw blood line 20 carries blood, for example arterial blood, from the patient 92 to a filter 30. A membrane in the filter 30 allows waste products such as urea and other undesirable metabolic byproducts that are blood contaminants together with water to pass through the filter membrane to the waste side of the filter 30 and out a side port 40 into a waste line 50. The waste line 50 drains the waste filtrate 61 into a waste container 60. The filter membrane does not permit blood cells and higher molecular weight proteins to pass through with the waste filtrate and thus concentrated, purified blood passes out the filter top port 70. The fluid volume lost as waste filtrate during the hemofiltration process must now be replaced in the concentrated, purified blood to return the blood to its proper physiologic concentration. Accordingly, a measured volume of purified replacement fluid ("RF") 81 from a purified fluid reservoir 80 is added to the filtered blood in an amount equal to the volume of waste filtrate removed during the hemofiltration process. A fluid balancing system (not shown in FIG. 1) that measures the waste filtrate removed and then dispenses the proper volume of replacement fluid needed is located inside the hemofiltration unit 1. Systems and devices for fluid balancing have been described in U.S. patent application Ser. No. 09/513,773, filed Feb. 25, 2000, the contents of which are incorporated herein in their entirety by reference. The replacement fluid flows from the replacement purified fluid reservoir 80, through the replacement fluid line 10, to the balancing system in the hemofiltration unit 1. The reconstituted blood, now consisting of the concentrated, purified blood and the measured amount of replacement fluid, is returned via the return blood line 90, for instance a venous line, to the patient 92.

Figure 2A:
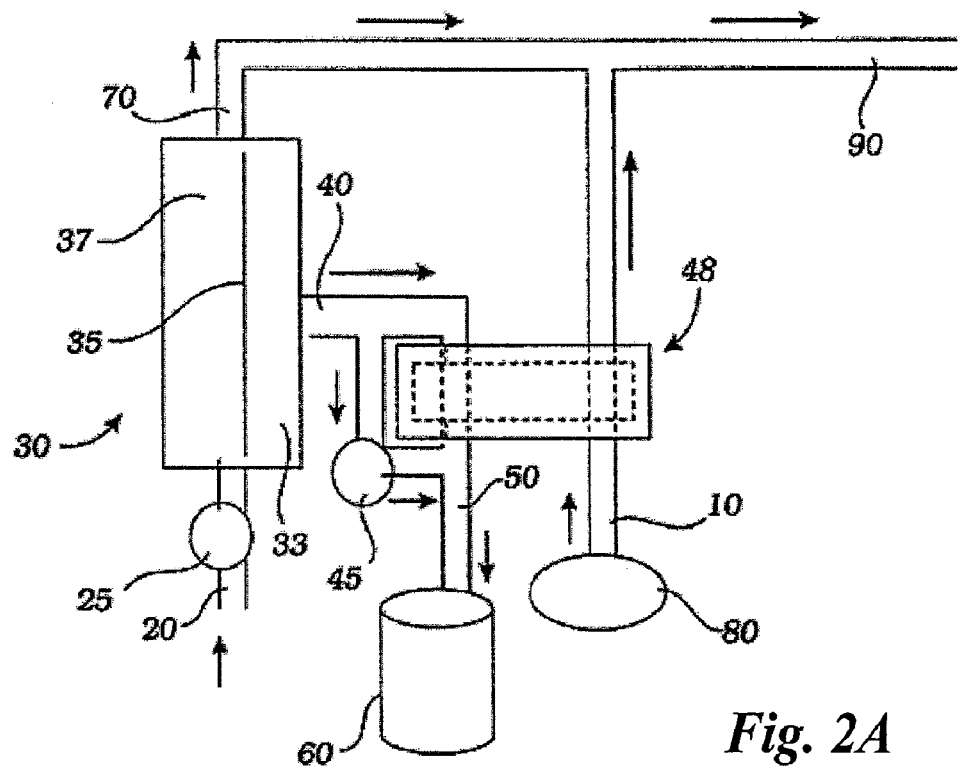
FIG. 2A is a schematic of the embodiment of FIG. 1, performing hemofiltration therapy.

FIG. 2A shows a schematic representation of the hemofiltration process. A draw blood line 20 carries blood from the patient to the filter 30. The blood pump 25 pushes the blood through the filter, and the pressure differential due to the positive pressure of the blood drives the blood across the membrane. A balancing system 48 meters the waste or blood, water, and contaminants through the membrane 35 of the filter 30, metering out the blood, water, and contaminants into the waste side 33 of the filter and allowing concentrated purified blood to pass out the clean side 37 of the filter and into the filter top port. 70. The waste filtrate exits the waste port 40 of the filter 30 and passes into the balancing system 48. Purified replacement fluid flows from the purified replacement fluid reservoir 80 through the replacement fluid line 10 to the balancing system 48 where a measured amount of purified replacement fluid equal to the amount of waste filtrate passed through the balancing system 48 is allowed to combine with the concentrated blood in the return line 90 and return to the patient. The waste filtrate that has passed through the balancing system passes through the waste line 50 and into the waste container 60.

If the therapy requires hemofiltration and ultrafiltration, then an ultrafiltration pump 45 removes excess fluid from the patient's blood and dumps the excess fluid into the waste container 60. This excess fluid removed by the ultrafiltration pump 45 does not pass through the balancing system and thus is not matched by an equal amount of replacement fluid. The system may use additional pumps such as a waste pump and a replacement fluid pump as part of the fluid balancing system to assist the proper fluid flow through the system.

Figure 3:
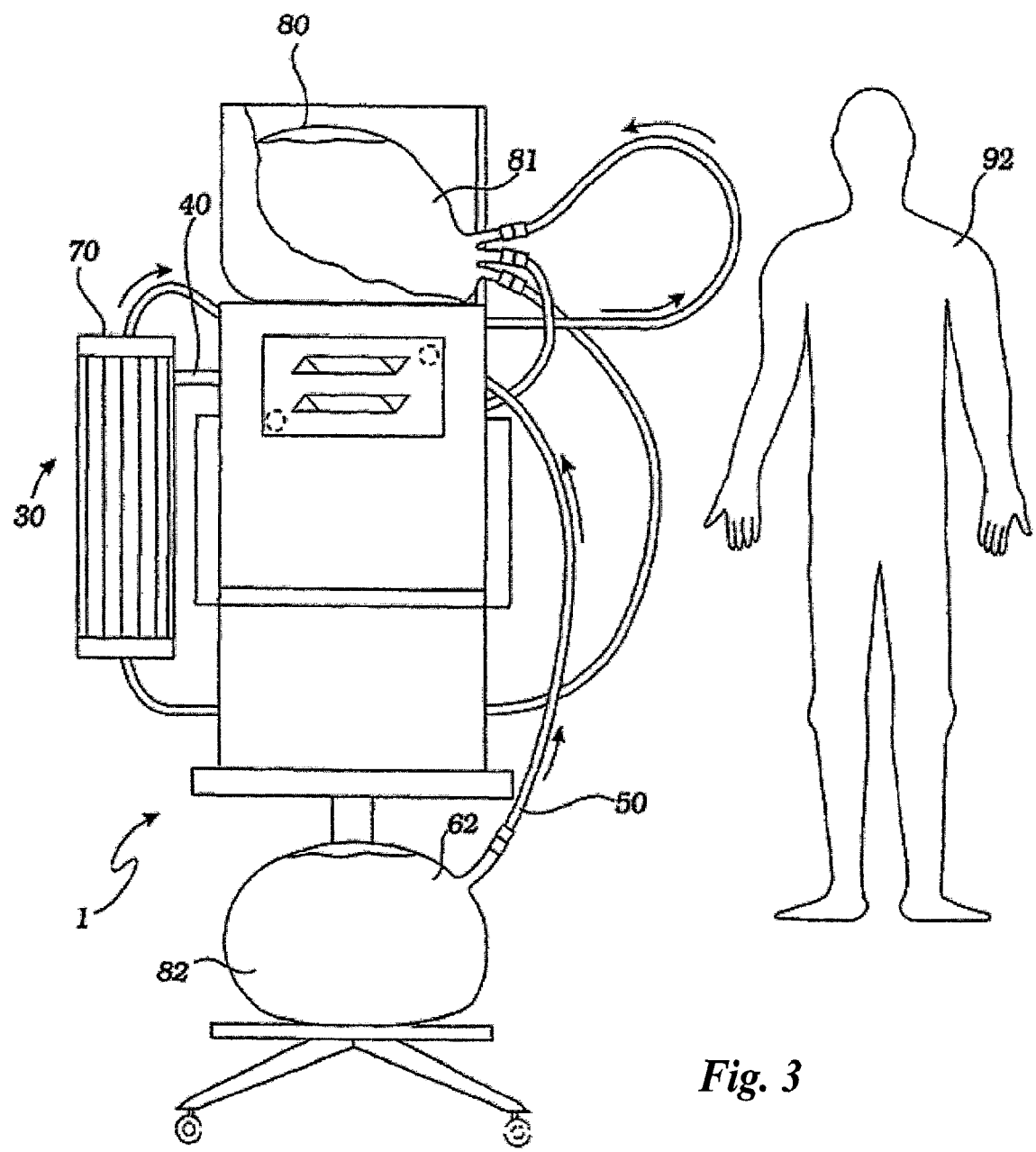
FIG. 3 is an embodiment of a hemofiltration unit operating in the reverse pumping mode used for solution sterilization

FIG. 3 shows an embodiment of the present invention prior to connection to the patient 92 to perform therapy. The hemofiltration unit 1 is configured to convert a solution of suitable electrolyte concentration for use as a replacement fluid 82, for example dialysate, in a container 62 to purified replacement fluid 81 that is pumped to a container adapted to hold the purified fluid, such as a purified fluid reservoir 80, via a filtration sterilization process. While the solution 82 to be converted will have the proper electrolyte concentration required of replacement fluids, there is a concern that the solution will include pyrogenic material, for example pathogens such as bacteria, endotoxins, and thus not be sufficiently pure to be injected into a patient as a replacement fluid. Thus, the hemofiltration unit can be used to filter the solution to remove pyrogens and to prepare safe replacement fluid for a subsequent hemofiltration procedure by running the appropriate pump in the hemofiltration unit in reverse of the pumping mode used for conventional hemofiltration. In a preferred embodiment, the hemofiltration unit is adapted to receive certain disposable components including a fluid pumping and balancing system as more fully explained herein.

Figure 2B:
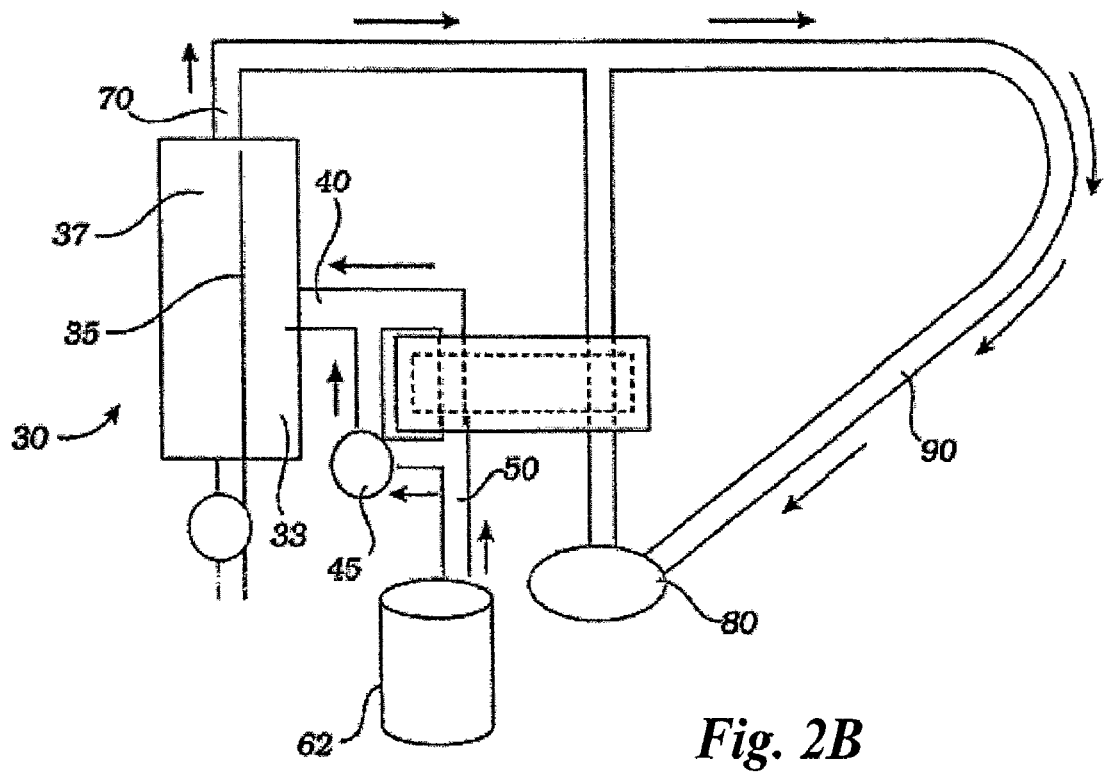
FIG. 2B is a schematic of the embodiment of FIG. 3 performing solution sterilization.

FIG. 2B shows the fluid sterilization process schematically. A pump in fluid communication with the fluid container 62, for instance an ultrafiltration pump 45, is run in reverse of the direction that the pump is conventionally run during ultrafiltration therapy to draw fluid from the container 62 up through the waste line 50 and into the waste side 33 of the filter 30 via the waste port 40. The pump 45 forces the fluid through the filter membrane 35 into the clean side 37 of the filter. Because the pyrogenic material in the fluid, for instance bacteria and endotoxins, are mostly larger than the pore size of the filter membrane 35, such material in the fluid remains on the waste side 33 of the filter. The filtered fluid, now rendered safe, emerges as purified replacement fluid from the top port 70 of the filter and flows through the return blood line 90 into the purified replacement fluid reservoir 80. Preferably, the filter is one that reduces the rate of endotoxins to very low levels. For example, for hemofiltration, an endotoxin rate of 0.03 EUs/ml. is preferred.

Figure 3A:
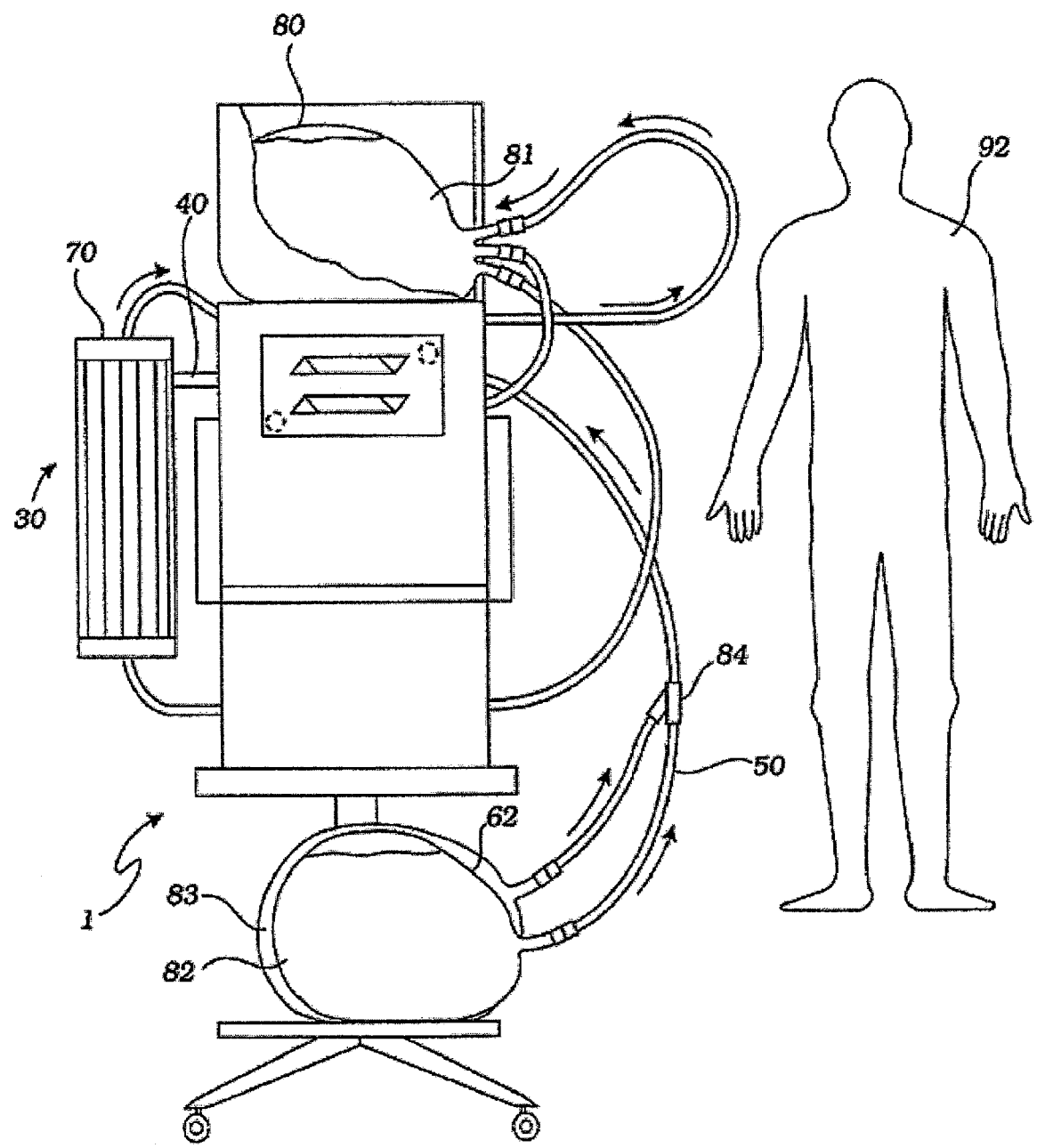
FIG. 3A depicts an embodiment of a hemofiltration unit used to mix dialysate.

In other methods, the user mixes the dialysate and then sterilizes it as shown in FIG. 3A. A first container 82 of concentrated electrolytes, e.g., any one or more of sodium lactate, potassium, calcium, magnesium chloride, sodium chloride, bicarbonate and/or other appropriate salts, and/or other elements, is connected to Y-connector 84. A second container 83 of water, ringers lactate, or saline is also connected to the Y-connector. The two solutions are then mixed as they pass through Y-connector 84 and then pass through the filter.

The hemofiltration unit automatically primes the remainder of the fluid pathway when all of the replacement fluid is transformed into purified replacement fluid. The priming process is described more fully herein.

Once the fluid pathway is primed, the hemofiltration unit is ready to be connected to the patient for renal replacement therapy. Referring again to FIGS. 1 and 2A, the blood pump 25 pumps the patient's blood through the filter 30, the balancing system 48 meters fluid from the purified fluid reservoir 80, and the trapped bacteria on the waste side 33 of the filter pass into the container 60 along with waste blood water. In a preferred embodiment, the now-empty container 60 previously containing the solution 82 can now be used as a waste container for the hemofiltration therapy. A system using more than one filter can also be employed. Further, the system can be used to mix a concentrate solution with another solution.

While the embodiments shown are described for hemofiltration therapy, the devices and methods can be used for blood processing, infusive therapies, or any renal replacement therapy, for instance hemodiafiltration, and can also be used for hemodialysis. Moreover, while the hemofiltration unit described is a volumetric system, this method can be readily employed with active flow balancing control such as massmetric systems that use scales instead of balance chambers or flow meters or purely mechanical systems based on weight or volume.

In a preferred embodiment, the fluid pumping and balancing system and optionally other elements may be preconnected, prepackaged, sterilized and sealed by the manufacturer into a disposable unit such as a kit to reduce touch contamination that can be introduced during set-up of the fluid sterilization process. A renal therapy unit is adapted to receive the kit, which is releasably coupled to the unit, to form a system for batch sterilization of replacement fluid and subsequent renal replacement therapy using the purified fluid. Following therapy, the kit may be removed and discarded and a new kit can be installed for a subsequent fluid sterilization and therapy procedure.

Figure 4:
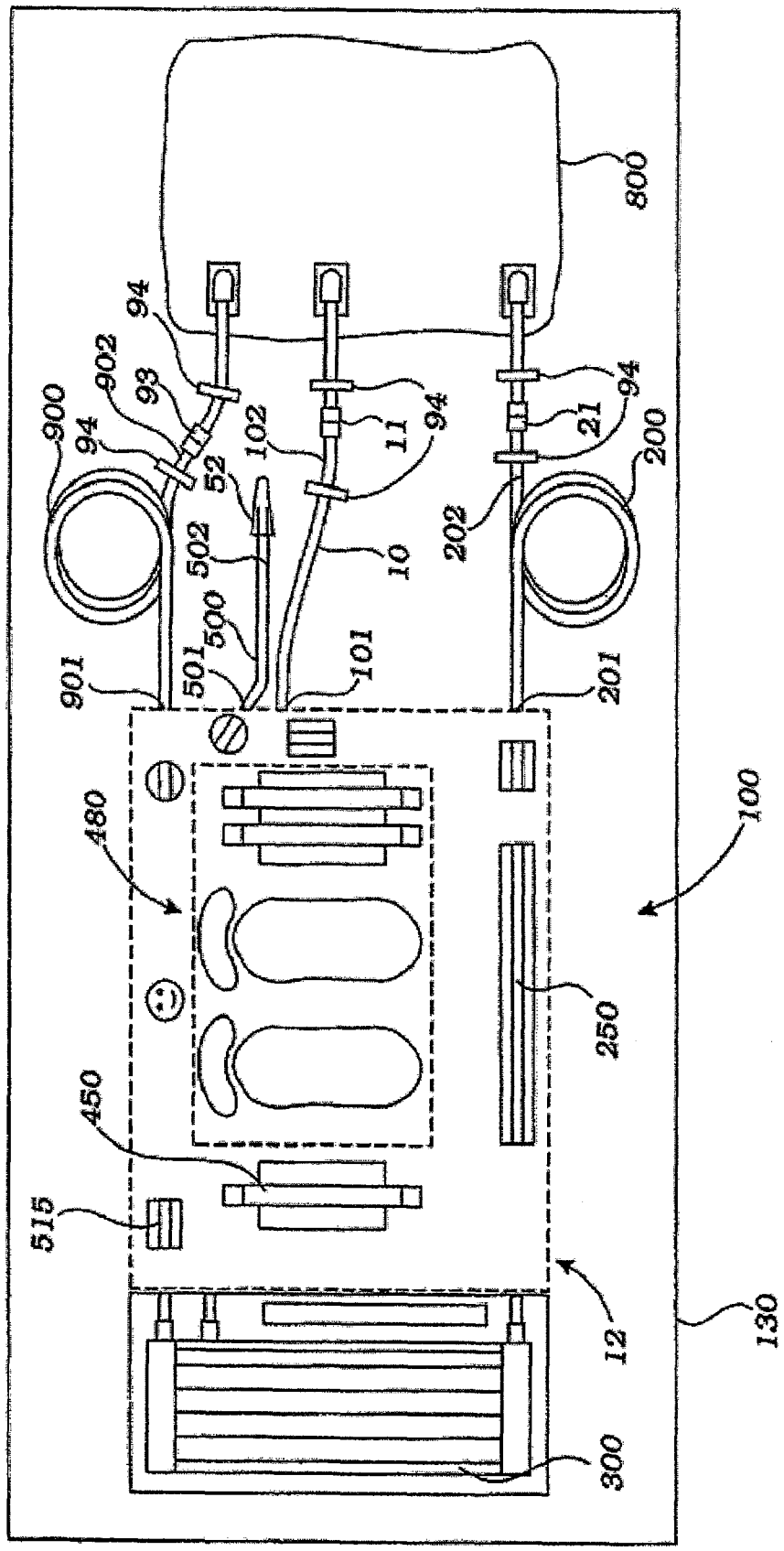
FIG. 4 is another embodiment of a disposable unit adapted to couple to a hemofiltration unit for solution sterilization, priming, and subsequent hemofiltration therapy.

FIG. 4 shows an embodiment of a pre-connected, disposable fluid management kit 100. The embodiment includes a filter 300, for example a hemofilter, and a purified fluid reservoir 800 connected to a fluid pumping and balancing system 12 through various tubes or lines 900, 10, 200. A first end 901, 101, 201 of each tube 900, 10, 200 is coupled to the fluid pumping and balancing system 12 and a second end 902, 102, 202 of each tube 900, 10, 200 is releasably coupled to the purified fluid reservoir 800 via connectors 93, 11, 21. Manual clamps 94 may also be used to control fluid flow when disconnecting lines. A waste line 500 has a first end 501 coupled to the fluid pumping and balancing system 12 and a second end 502 removably sealed by a cap 52. In the embodiment of FIG. 4, the fluid management kit includes a filter 300 in fluid communication with the pumping and balancing system. 12. The pre-coupled, disposable components of the fluid management kit are sterilized by the manufacturer and sealed in a suitable container 130 to guard against contamination. The container 130 may be a poly bag, TYVEK™, paper or other suitable material. The sterilization process used by the manufacturer may be of any conventional method used for sterilizing medical equipment such as gamma irradiation, chemical sterilant such as ethylene oxide, steam, e-beam or the like. The fluid pumping and balancing system 12 of the embodiment of FIG. 4 includes a blood pump 250, an ultrafiltrate pump 450, a fluid balancing system 480, and a venous air detector 515. The fluid balancing system 480 illustrated in the embodiment is a volumetric system, however it could also be gravimetric flow meters or other means of fluid balancing. The components of the fluid management kit may be connected to form a fluid pathway in any conventional structure used for hemofiltration and ultrafiltration such as the structures shown in the embodiments of FIGS. 1-3. Similarly, the hemofiltration filter 300 may be integrated into the fluid pathway in any conventional structure. In certain embodiment, the hemofiltration filter is not part of the disposable kit.

In the embodiment of FIG. 4, the purified fluid reservoir 800 is releasably coupled to the fluid pumping and balancing system 12 through a blood return line 900, a purified replacement fluid line 10 and a draw blood line 200 through connectors 93, 11, and 21. The connectors 93, 11, and 21 can be Luer connectors, proprietary connectors or any other connectors that will provide a hermetic seal that can be decoupled by a user. The purified fluid reservoir 800 may be of any size required by the therapy, but preferably between 1 and 75 liters and most preferably between 5 and 50 liters, generally approximately 20 liters. The replacement fluid container line 500 can later be used as a waste line during hemofiltration.

Use of the pre-packaged, sterilized fluid management kit greatly reduces the risk of touch contamination. For instance, in the embodiment of FIG. 4, the only connection that must be made by the user during set up is the connection of the replacement fluid container to the waste line 500. Replacement fluid is commonly provided in one-liter bags, thus requiring up to 50 of more connections to sterilize a sufficient amount of fluid depending on the prescribed therapy. In the embodiment of FIG. 4, all of these connections are made on the waste side of the filter, and accordingly any contamination introduced by the connection procedure is filtered out as the solution moves through the system to the purified fluid reservoir 800 during batch sterilization.

Figure 5:
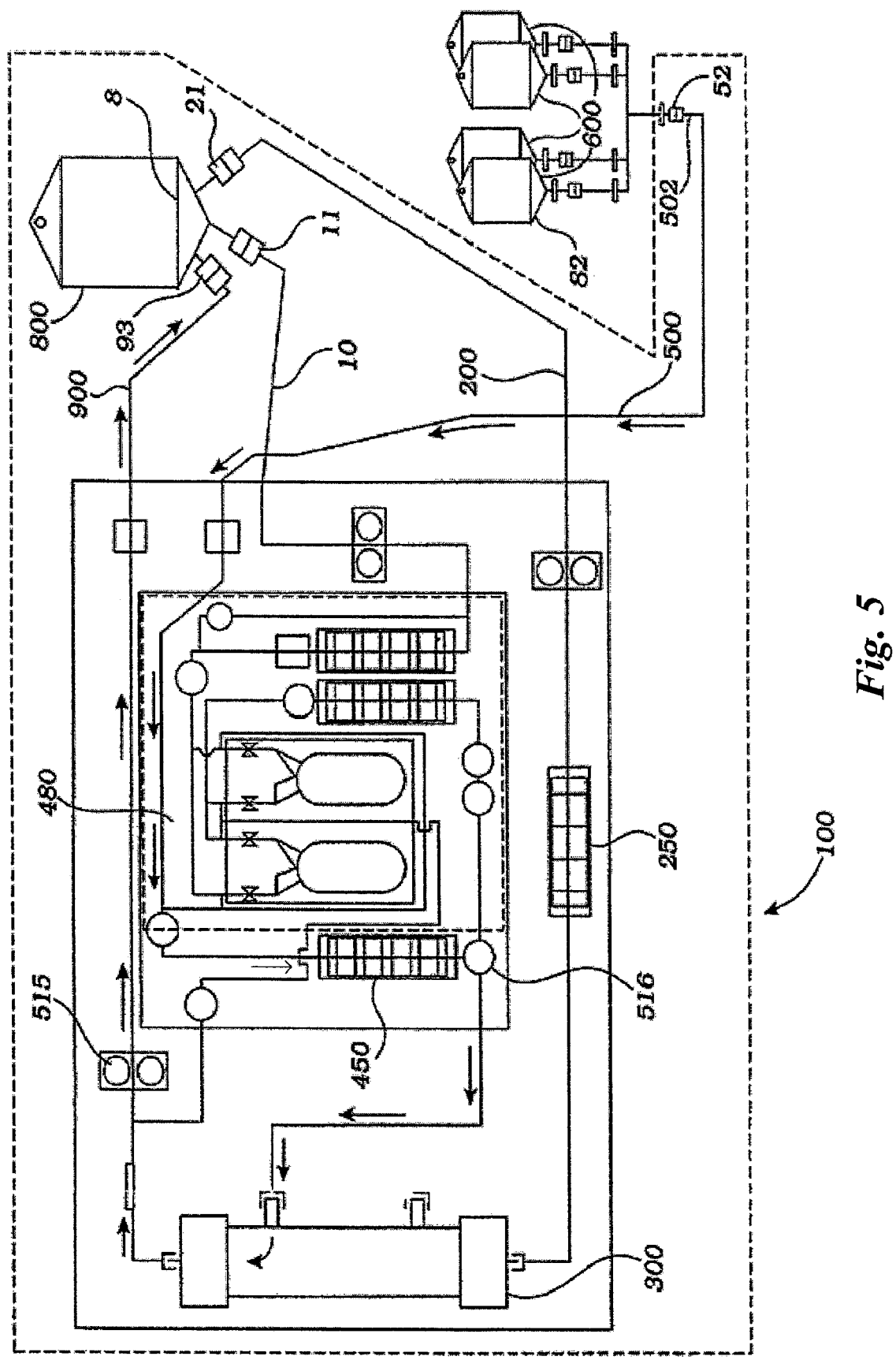
FIG. 5 is an embodiment of a hemofiltration unit performing solution sterilization demonstrating the fluid flow paths.
Figure 7A:
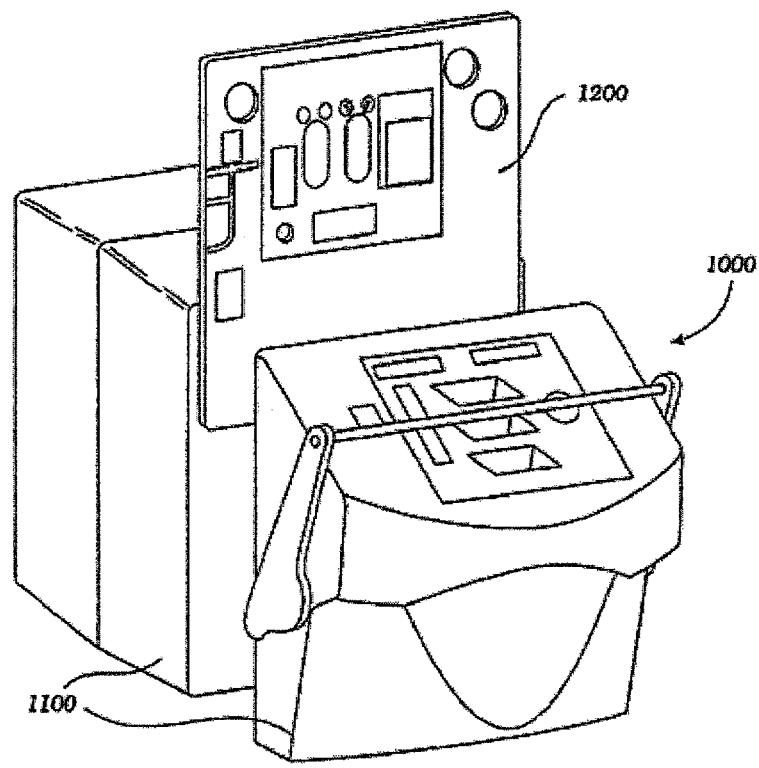
FIG. 7A is an embodiment of a renal replacement therapy system (without tubing) showing the installation of a fluid management kit in a hemofiltration unit adapted to receive the kit.
Figure 7B:
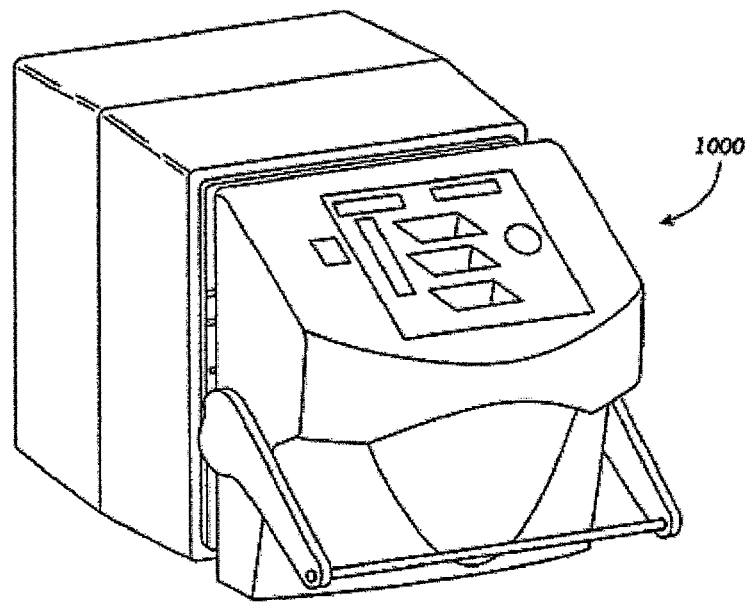
FIG. 7B shows the embodiment of the system of FIG. 7A with the kit fully installed (without tubing).

FIG. 5 shows a schematic of the fluid flow of the fluid management kit 100 of the embodiment of FIG. 4 in use in a system for batch sterilization of replacement fluid and subsequent renal replacement therapy, where the system includes the hemofiltration unit fitted with a disposable fluid management kit. The system is best seen in FIGS. 7A and 7B, where the system 1000 for batch sterilization of replacement fluid and renal replacement therapy using the purified fluid includes a renal replacement therapy unit 1100 adapted to releasably receive a sterilized fluid management kit and a purified fluid management kit 1200 (tubing and bags not shown). FIG. 7A shows the installation of the kit 1200 into the unit 1100. Returning now to FIG. 5, the fluid flow illustrates the batch sterilization process. The second end 502 of the waste line 500 has been releasably coupled to the replacement fluid containers 600. All of the other fluid connectors 93, 11, 21 have been preconnected by the manufacturer and thus are not a source of touch contamination during set-up. Only one pump 450 runs during filtration. All other pumps and the balancing system are dormant during filtration. Filtration continues until the entire batch has been processed.

Figure 6:
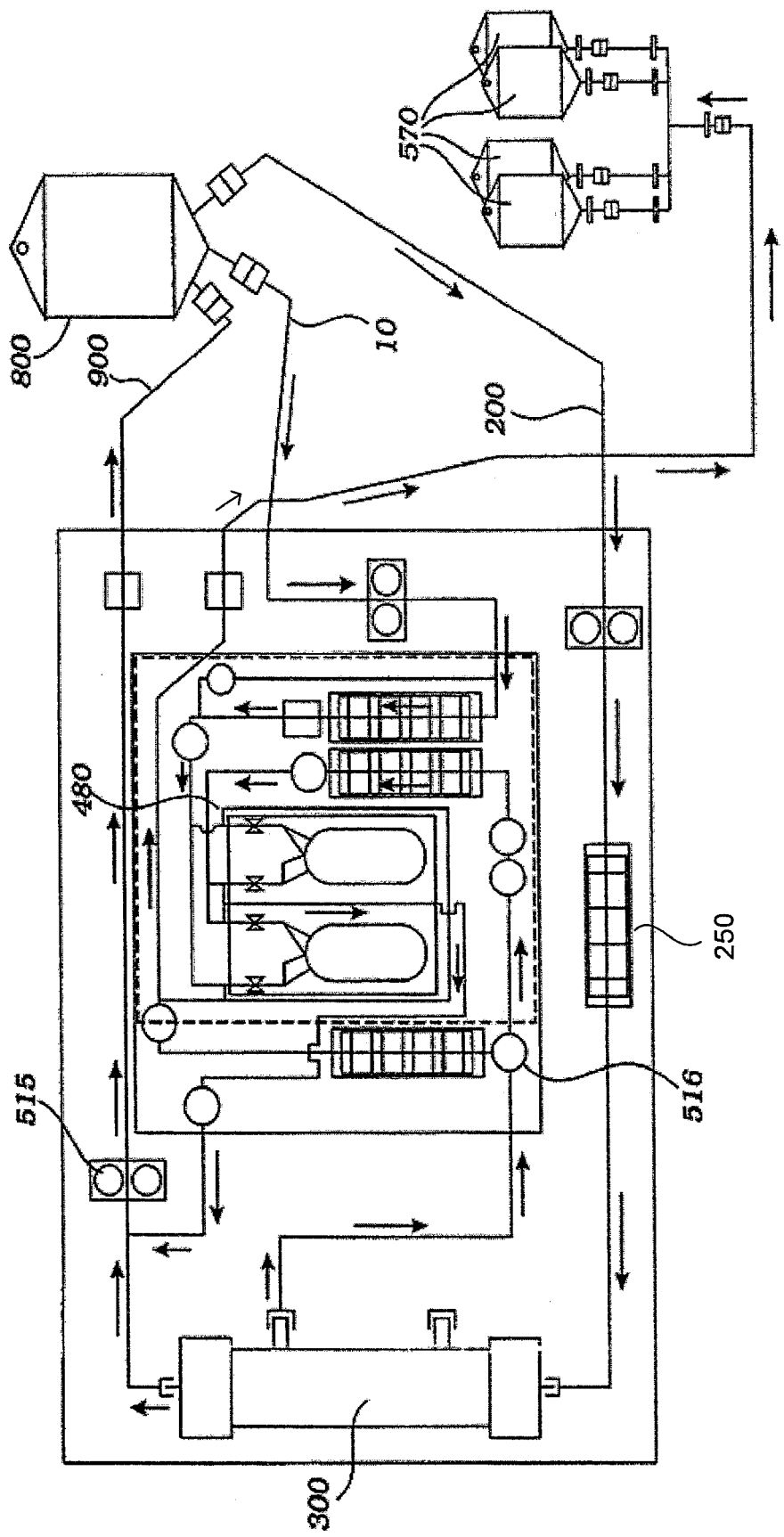
FIG. 6 is an embodiment of a hemofiltration unit in priming mode.

During replacement fluid sterilization, the pump 450, which in this embodiment is the ultrafiltration pump, runs in reverse (a second direction) of its conventional therapeutic pumping direction (a first direction) through filter 300 until the containers 600 of replacement fluid are empty. The emptying of the container results in air pumped into the filter, which is sensed by the venous air detector 515, best seen in FIG. 4. When the venous air detector 515 senses the presence of air, software in the hemofiltration system triggers the pump 450 to reverse the pumping direction to the first direction and to prime the system including the filter. Alternatively, the pump 450 may be stopped and the balancing system turned on. This pumps fluid first direction pumps fluid from the purified fluid replacement reservoir 800. This priming process is shown in FIG. 6. Since the blood return line 900, the draw line 200 and the replacement fluid line 10 are all connected to the purified replacement fluid reservoir 800, fluid can-be drawn out and air pushed into the reservoir 800 where it floats out of solution. The pump 250 rotates in the forward, or first, pumping direction, metering fluid from the bag 800 and forcing air into the bag 800 from the return line 900. Fluid is drawn-through the replacement fluid line 10 and into the fluid balancing system 480 forcing air out into the venous return line 900. Purified replacement fluid is pushed back across the filter 300 to the waste side of the filter and dumping a minimum of fluid into the former replacement fluid containers, now the waste containers 570. Because the reservoir 800 of purified replacement fluid acts as a bubble trap, the hemofiltration system, exclusive of the bag, is primed and free of air.

An integrity test can be performed on the filter to verify that the replacement fluid was properly filtered during sterilization. The test, substantially similar to that used in manufacture of the filter itself, measures the partial pressure of the wet filter using the air from the arterial line as the test medium. The replication of the manufacturer's test assures that the filter is leak free and thus the filtered fluid is purified and safe to use as a replacement fluid.

In certain embodiments, a blood leak detector 516 can be incorporated into the fluid pumping and balancing system and used as a redundant test of filter integrity. If the filter demonstrates a leak after the patient has been connected, the blood leak detector will alarm.

Once a test of filter integrity is successfully performed and the system has been primed as previously described, the unit is ready for renal replacement therapy, for instance hemofiltration or hemodiafiltration. The second end of each of the draw and return lines is decoupled from the purified replacement fluid reservoir and each is releasably coupled to the appropriate vascular access of the patient and renal replacement therapy is initiated. The vascular access can be a native fistula, a synthetic graft, a catheter a subcutaneous port or other conventionally used method.

Figure 8A:
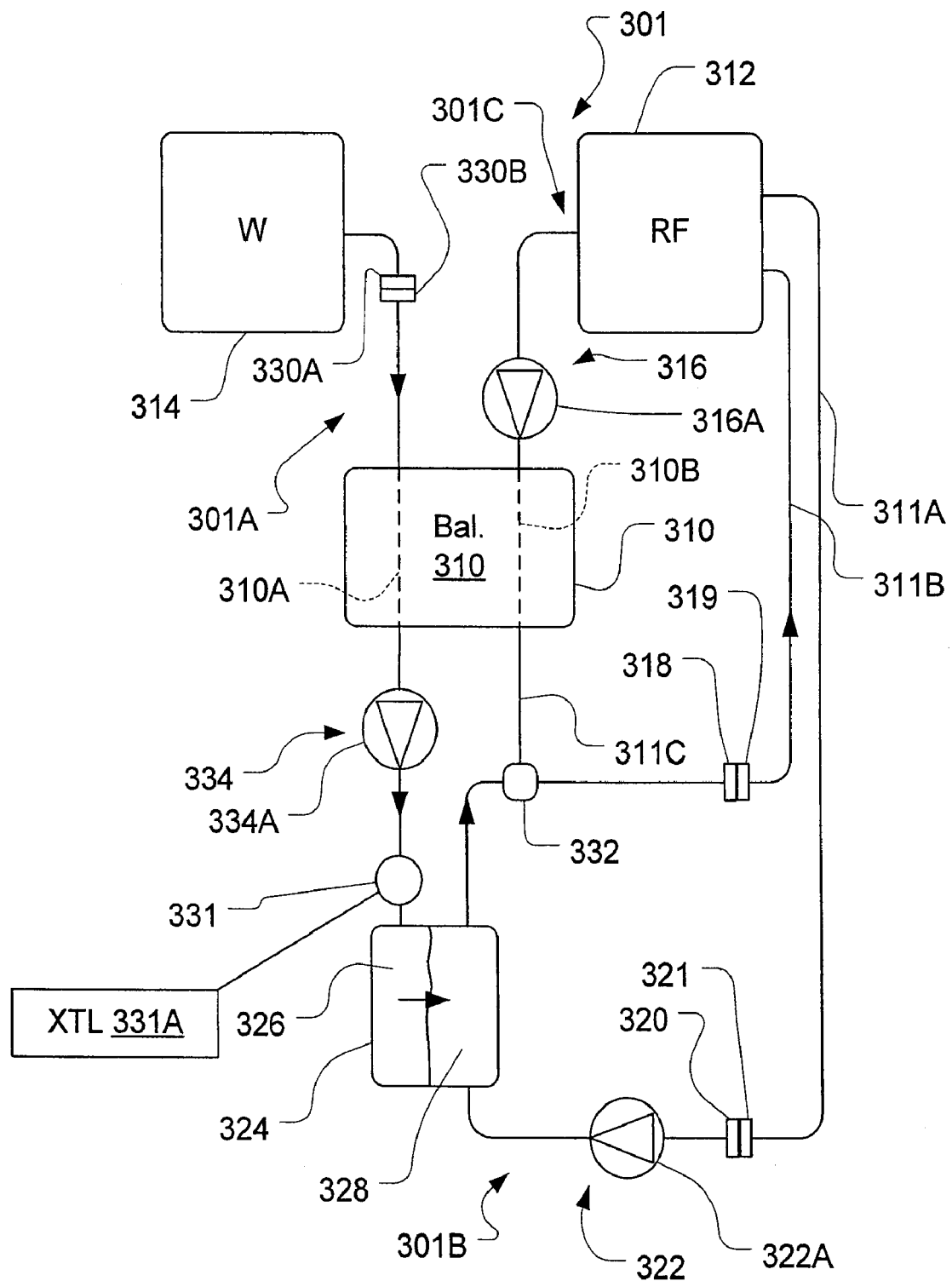
FIG. 8A illustrates a hemofiltration system without waste fluid bypass configured for generation of purified replacement fluid.

Referring to FIG. 8A, in a hemofiltration embodiment where no ultrafiltrate pump is available or where it is preferred to use a pump other than an ultrafiltrate pump, a waste fluid pump 334 is used to convey raw replacement fluid through a filter 324 for preparation of a batch of purified replacement fluid. Note that in this embodiment, a balancing mechanism 310 must be one that permits a negative pressure to be transmitted through it to the source fluid container 314 in order for this to work. For example, the balancing mechanism 310 may incorporate an internal bypass to permit the waste pump 334 to draw raw fluid through the balancing mechanism 310 waste side 310A. Alternatively, a six-way valve or set of valves may be used to reverse flow such that positive pressure is always applied to the balance mechanism or, if not required, a simple flow direction reversal. A connector 330A is provided to permit connection of the raw fluid reservoir 314. The waste fluid pump 334 pumps in the direction shown to convey fluid through the filter 324 then through any and/or all of the lines 311A, 311B, and 311C via junctions 332 and couplings 318/319 and 320/321. Purified replacement fluid is collected in a replacement fluid container 312. As in previous embodiments, preferably, all connections are permanent except couplings 318/319 and 320/321, which are only uncoupled momentarily for connection to a patient access, and 330A/330B. The circuit guards against contamination because the latter coupling is isolated from the replacement fluid container 312 and all the lines 311A, 311B, and 311C which might introduce contaminants into the patient bloodstream.

A pressure sensor 331 may be provided upstream of the filter 324 and downstream of the pump 334. The pump 334A may be operated during preparation of replacement fluid and halted intermittently while a controller 331A records a pressure relaxation profile output by the pressure sensor 331. Any changes in the shape of the curve may be determined by suitable calibration procedures to correspond to a possible loss of integrity of the filter 324. If a change in the pressure relaxation curve goes beyond some suitable limit, an alarm may be activated and the replacement fluid preparation operation halted by the controller 331A. One example of a parameter for monitoring is to provide a programmable controller to fit each real time data set to an exponential to generate a decay constant, which may be stored to create a stored record. The record may be queried to detect any changes in the decay constant or change in a rate of change if the decay constant that may be used as an indication of a loss of integrity. The integrity check may also server to ensure the integrity of the waste portion of the fluid circuit as well.

Note that if pumps 316 and 322 are of a type that can selectively permit the free backflow of fluid, fluid may pass through all of the lines 311A, 311B, and 311C during purified fluid preparation. Alternatively, the pumps 316 and 322 may be bypassed and fluid passed through line 311B alone.

Figure 8B:
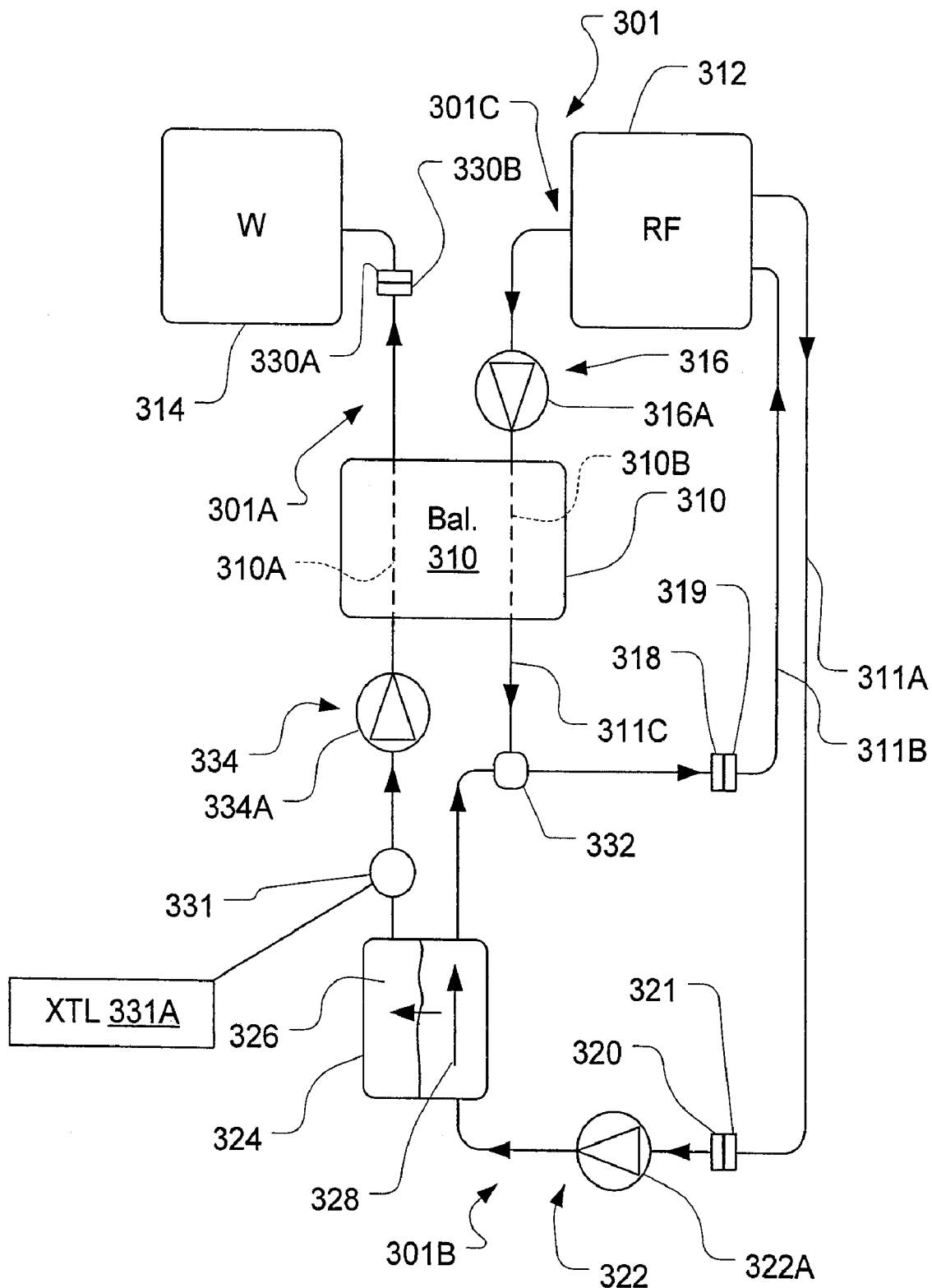
FIG. 8B illustrates a hemofiltration system without waste fluid bypass configured for priming with purified replacement fluid.

Referring now to FIG. 8B, the embodiment similar to that of FIG. 8A, is illustrated as it operates during a priming mode. As explained earlier, no connections are newly made or broken in going from preparation mode of the previous figure and priming mode as in the present figure. Purified fluid is now pumped by a replacement fluid pump 316 through the balancing mechanism 310 replacement fluid side 310B. At the same time, blood pump 322 draws purified fluid and pumps it through the purified side 328 of the filter 324 where part goes into the waste side 326 and part runs through junction 332 back to the replacement fluid container 312. The waste pump 334 may be run at a slow rate to permit a small amount of fluid to be metered through the waste side and into the waste receptacle 314, which during preparation mode of FIG. 8A served as the raw replacement fluid container. Note that during priming, the waste pump 334 runs in a direction opposite that used during preparation. In an alternative embodiment, the waste pump 334 may be such that it allows passive flow either selectively or permanently. Permanent passive flow capability may be provided by ensuring that the waste pump 334 provides less than a 100% seal. Selective passive flow capability may be provided by providing a controllable actuator to back an internal platen (used in peristaltic pumps) slightly away from the pump rollers of the peristaltic pump that is usually employed in medical systems.

Figure 8C:
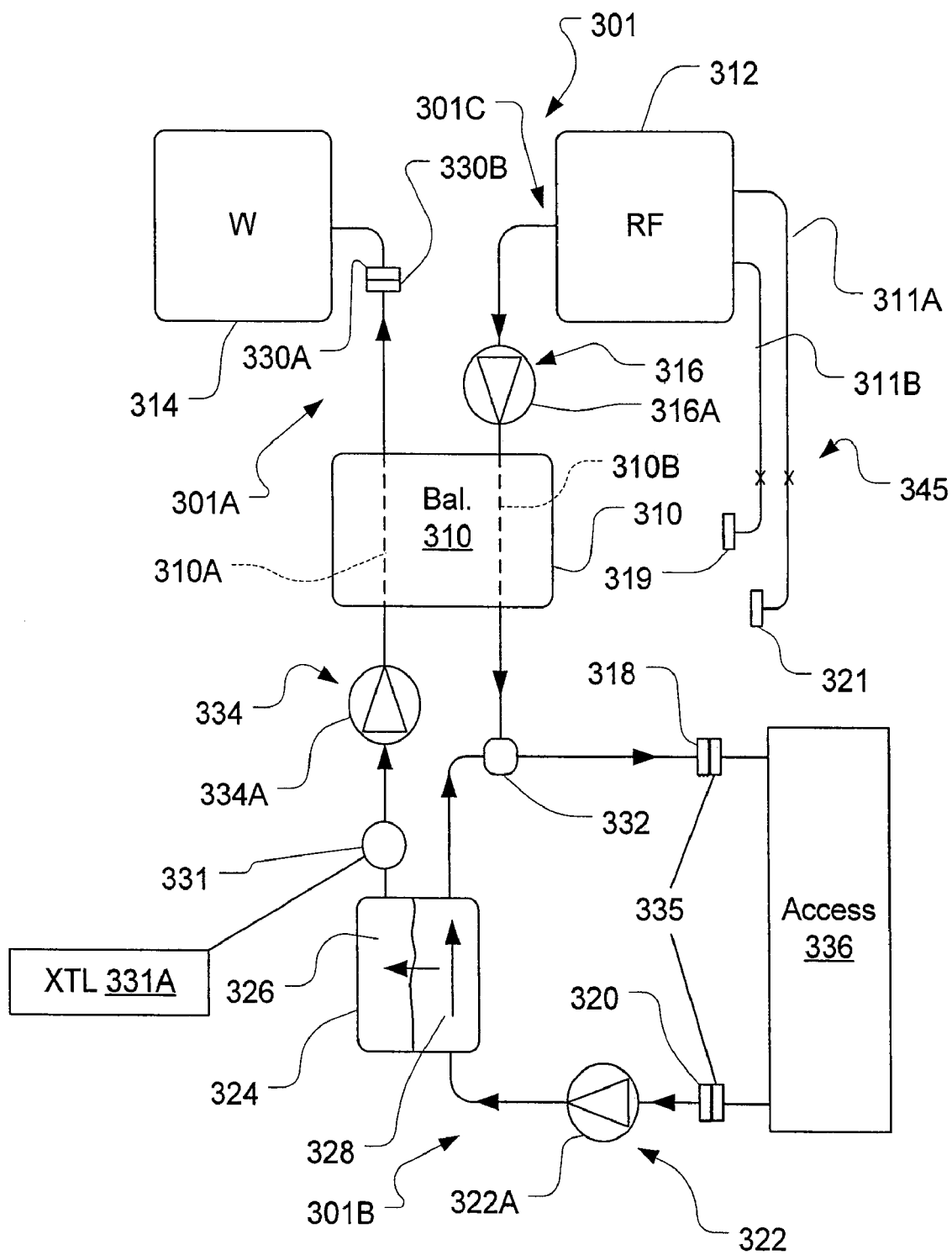
FIG. 8C illustrates a hemofiltration system without waste fluid bypass configured for treatment.

Referring now to FIG. 8C, the hemofiltration system of the foregoing embodiments is shown in a treatment mode. The connections 318/319 and 320/321 are broken and connected to connectors 335 of a patient access 336. Before beginning operation of the pumps 316, 322, and 334, lines 311A and 311B are clamped to prevent fluid leaking or contamination. To treat, pumps 316, 322, and 334 all operate in the same directions as in the previous embodiment. Blood is drawn from the patient access 336 and flows through the filter 324 where waste is drawn by waste pump 334. For each unit of waste passing through the balancing mechanism 310, an equal unit of replacement fluid is pumped into junction 332 and ultimately into the patient access for reinfusion. To draw down a net volume of fluid in a patient in this type of system which lacks a bypass, the balancing mechanism may be configured to negatively bias the flow of replacement fluid appropriately by some other means such as numerical control, mechanical means, etc. A number of such means are known. Also, the waste pump 334 may be run for a period of time after stopping the replacement fluid pump 316 and placing the balancing mechanism in configuration that permits passive flow through it. For example, this may be done by opening the balancing chamber valves in the waste fluid circuit in the balancing mechanism disclosed in U.S. Pat. No. 6,554,789, which is hereby incorporated by reference as fully set forth in its entirety herein.

Figure 9A:
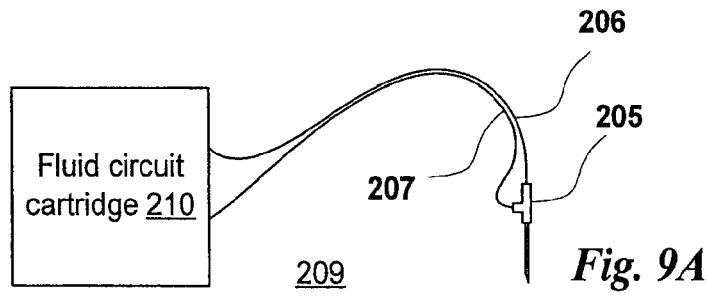
FIG. 9A illustrates a fluid circuit with a double lumen access needle permanently attached to the venous line.
Figure 9B:
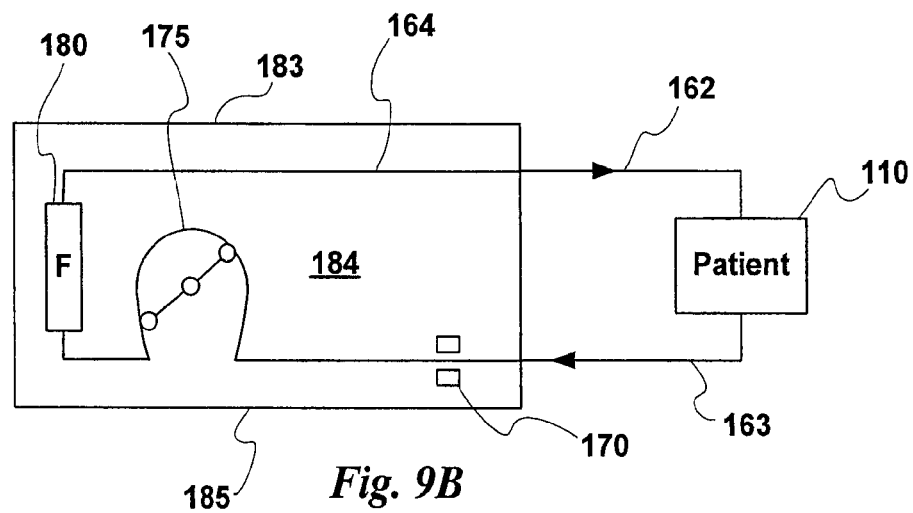
FIG. 9B illustrates some details of the device of FIG. 9A in a use context.

FIG. 9A illustrates a fluid circuit portion 210 in the form of a cartridge and FIG. 9B shows the embodiment of FIG. 9A in use in a blood treatment machine 183. Examples are illustrated in U.S. patent application Ser. No. 09/513,773, which is hereby incorporated by reference as if fully set forth in its entirety herein.

In the field of extracorporeal blood treatment, it is the general practice to provide connectors for connecting and disconnecting the venous line from the access device. Thus, the embodiment of FIGS. 9A and 9B shows a consumable component that may be provided for treatment in which a permanent connection exists between the venous line 206 and a venous channel of the access device 205 of a consumable fluid circuit or portion thereof. An arterial line 207 may or may not be connected to the needle 205 by a detachable connector. FIG. 9A illustrates a cartridge portion 210, but the consumable device of FIG. 9 may be packaged in a form other than a cartridge, as is known.

Figure 10:
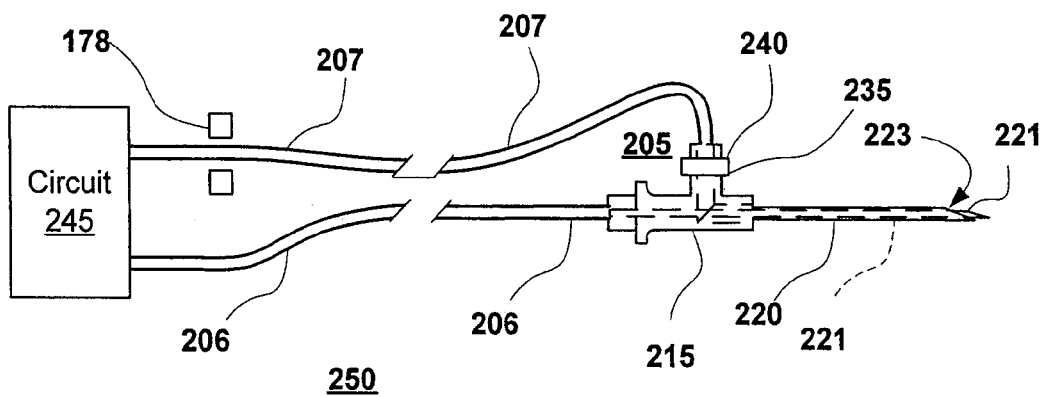
FIG. 10 illustrates details of the embodiment of FIGS. 9A and 9B.

Referring now also to FIG. 10, the venous line 206 is permanently connected to a body 215 by, for example, adhesive bonding, thermal welding, mechanical lock or some other means. In a preferred embodiment, the permanent connection runs at least to a point of the air sensor 178 in the blood treatment machine 245. Referring now particular to FIG. 9A, the permanent connection between the needle or catheter 205 may be ensured by providing the permanent arrangement as part of a fluid circuit 209 with a main portion 210 permanently attached to the venous line 206. Referring now particularly to FIG. 9B, the permanent connection is preferably continuous up to and including a pump portion of the circuit 175 and a first air sensor 170 ordinarily part of the blood treatment machine 183. This ensures that if any connections are improperly made, they can only happen in such a way as to cause air to be drawn in. Referring to FIG. 10, thus, a fluid circuit 250 defines a continuous and permanent connection from an entry point 223 up to an air sensor 178. The circuit may include various portions 245 which may include a filter 180 and other components for a blood treatment. Thus, the filter 180 (shown in FIG. 9B and embedded in portion 245 in FIG. 10), in a preferred configuration, is permanently attached and supplied with the fluid circuit 250.

Note that preferably the needle or catheter 205 is of such design that if the needle pulls out, there is no practical possibility that the venous line 206 could allow blood loss without air being sucked into the arterial line. The permanent connection is a part of this, but if the venous cannula extends further than the arterial cannula, this can be assured. In an alternative embodiment, both the venous 206 and arterial 207 lines are permanently connected to the double lumen access needle 215 thereby ensuring further against touch contamination.

Figure 11A:
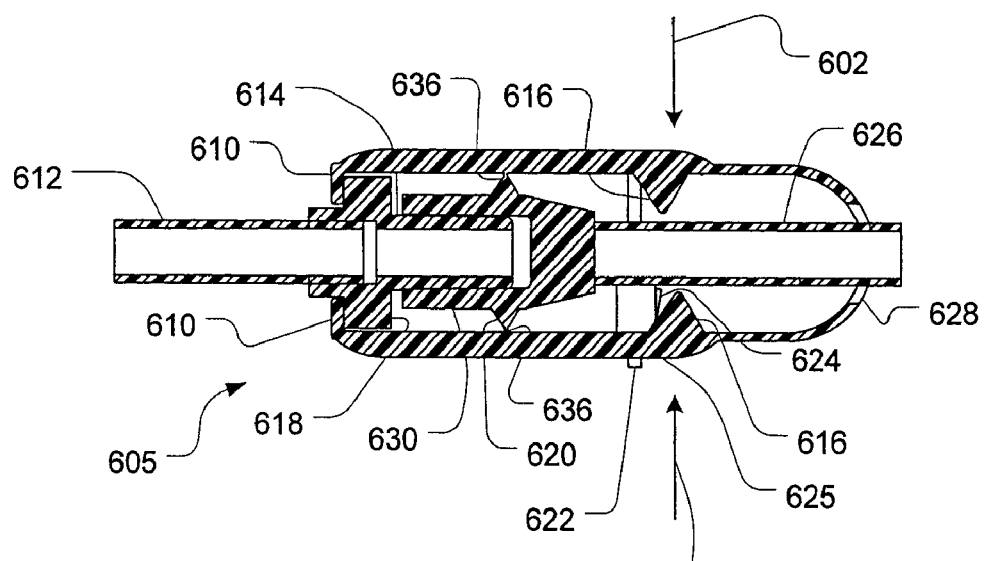
FIG. 11A illustrates a first embodiment of an automatically-self sealing connector.

Referring now to FIG. 11A, a connector 605 which disconnects a male luer 618 from a female 630 when a clamp 625 is pinched as indicated by arrows 602. The connector 605 may be used for connections 318/319 and 320/321 of FIGS. 8A-8C. When pinched, ridges 616 of the clamp 625 engage and compress a tube 626 passing through an opening 628 in clamp 625. Spines 614 and 618 pivot about living hinges 636 withdrawing hooks 610 from engagement with male luer 618. Thus, the male luer 618 cannot be disconnected from the female 630 without pinching off tube 626. To keep tube 626 pinched off, a tongue and pawl mechanism 624 and 622, such as commonly used in tubing clamps and common plastic wire ties may be used prior to disconnection, the tube 612 is preferably clamped to prevent leakage. Once disconnected, male luer 618 may be connected with a female luer connector (not shown) of a patient access (not shown). This ensures that there is no chance of air or pyrogens making their way into the RF container.

Figure 11B:
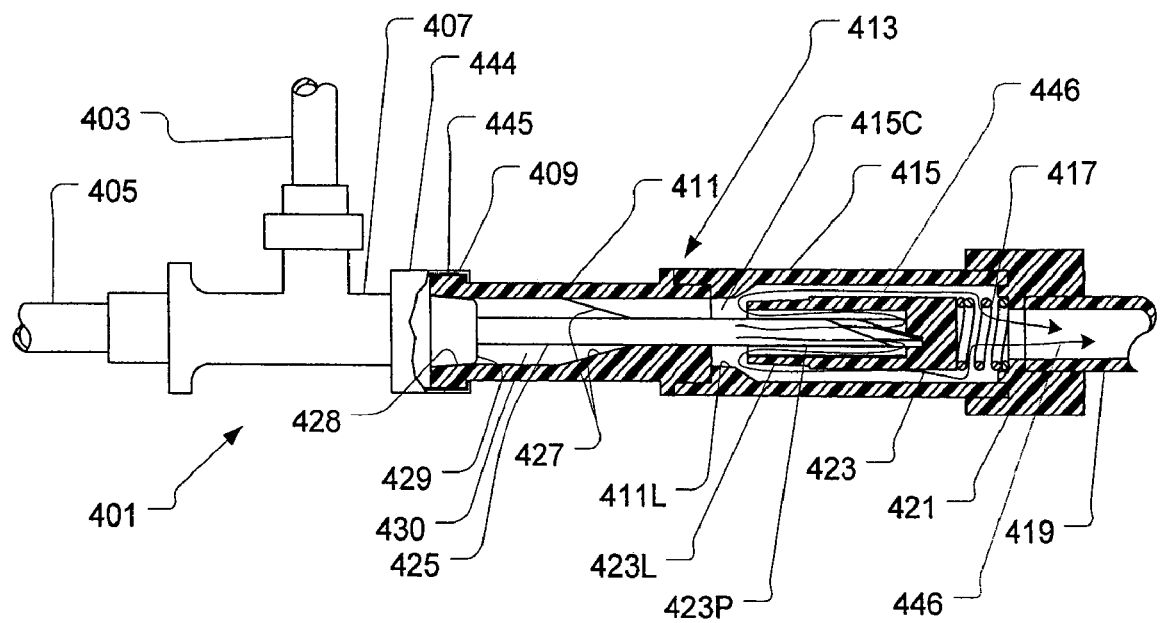
FIG. 11B illustrates a second embodiment of an automatically-self sealing connector with a combined double lumen access needle.

Referring to FIG. 11B, another connector 401 is configured to ensure a tube 419 is blocked prior to disconnection in preparation for treatment. The connection includes a double lumen access needle 407 which may be configured as discussed with reference to FIGS. 9A, 9B, and 10. The needle 425 fits snugly within a channel 430 inside a casing section 411. The needle is guided by vanes 427 which project axially such that the needle 425 is supported at the center of the casing section 411. The vanes permit fluid to flow around the needle 425. The casing section 411 is permanently attached to a casing section 415 which houses a cap 423 fitted over the end of needle 425. A tube connector 421 has a spring 417 that is positioned to help keep the cap in place when connector 421 is attached permanently to channel section 415. A tube 419 is permanently attached to the connector 421.

The needle 407 has a male luer 429 fitting that is inserted into a female luer fitting 428 in the casing section 411. The male and female luers 429 and 428 are held together by a peel-away compression band 409 that wraps over projecting portions 444 and 445 of the dual lumen access needle 407 and casing section 411, respectively. When the band 409 is peeled away from the projecting portions 444 and 445, the dual lumen access needle 407 may be withdrawn from the casing section 411.

The cap 423 has radial projections 423P that center the needle 425 within the cap 423 but allow fluid to flow from the end of the needle 425 and out of the cap 423. Thus, fluid may flow from either tube 403 or 405 through the needle 425, through an interior of the cap 423 through casing sections 411 and 415 and out through the tube 419 as indicated by arrows 446. Preferably, before the dual lumen access needle 407 is withdrawn from the casing section 411, the tubes 403 and 405 are clamped to prevent leaking. The dual lumen access needle 407 may be inserted into a patient access immediately after withdrawal from casing section 411.

The cap 423 has a male luer type fitting portion 423L at a base thereof. A female luer type fitting portion 411L receives the male luer type fitting portion 423L when the dual lumen access needle 407 is withdrawn from the casing section 411 of the connector 413 and the cap is pulled off the needle 425. As a result the 415C is plugged by the cap 423.

Figure 11C:
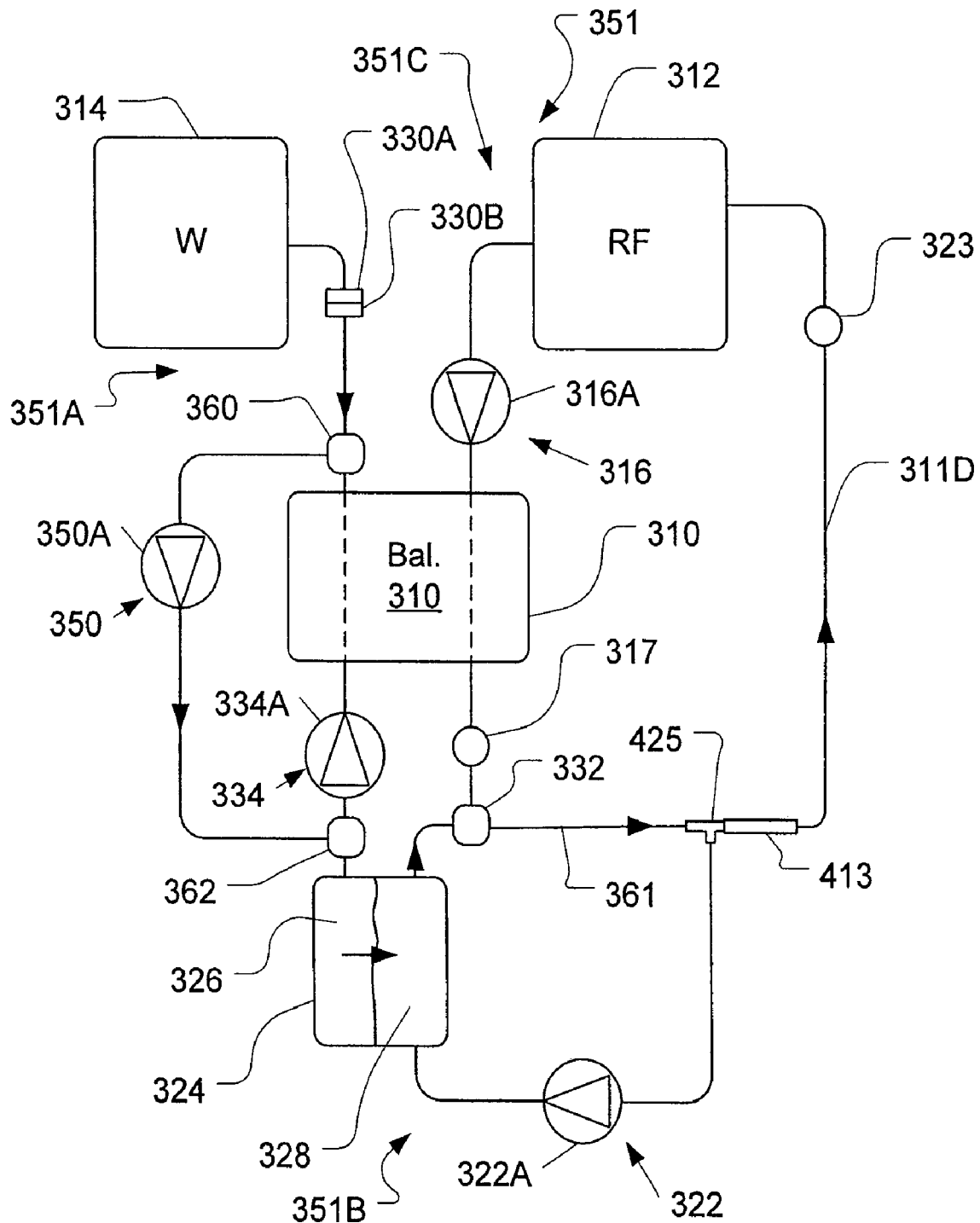
FIG. 11C illustrates the use of the embodiment of FIG. 11B with a fluid circuit during replacement fluid preparation.

The embodiments of FIGS. 11A and 11B may help to guard against contamination by preventing any backflow of fluid into the replacement fluid reservoir (e.g. 312 of FIGS. 8A-8C) of any of the foregoing embodiments. This is illustrated in FIGS. 11C and 11D which show the configuration of a representative embodiment of hemofiltration system in fluid preparation and treatment modes. During fluid preparation, the double lumen access needle 425 is inserted in the connector 413 and only ultrafiltrate pump 350 may be operated while the replacement fluid pump 316, the waste pump 334, and the blood pump 322 are idle. Raw fluid flows from a waste container 314 through connector 330A/330B through a junction 360, through an ultrafiltrate pump 350 running in reverse, through a junction 362, through a filter 324, through junction 332, through the double lumen access needle 425 and the connector 413, through the common line 311D, and into the replacement fluid container 312. As discussed above, the replacement fluid is purified and preferably left with an endotoxin level below 3 EU/ml. by the properties of the media provided in the filter 324.

Referring now to FIG. 11D, in priming mode, the replacement fluid pump 316 pumps fluid in a reverse direction into the replacement fluid container 312 while the blood pump 322 draws replacement fluid from the replacement fluid container 312 through the line 311D, through the connector 413, through the double lumen access needle 425, through the blood pump 322 through the filter 324, through the junction 332, through the replacement fluid side 310B of the balancing mechanism 310, to the replacement fluid pump 316. At the same time waste pump 334 draws fluid from the filter 324 via the junction 362 and pumps it through the balancing mechanism 310 waste side 310A and into the waste container 314 while the ultrafiltrate pump draws fluid from the junction 362 and pumps it through the junction 360 into the waste container 314. As discussed above, a continuous circulation through the replacement fluid container 312 provides a flow of substantial rate and duration to eliminate most of the air in the purified replacement fluid by allowing it to settle in the RF container 312. This is also discussed in U.S. Patent Application Ser. No. 60/386,483, entitled: "Last-chance quality check and/or air/pathogen filter for infusion systems," which is hereby incorporated by reference as if fully set forth in its entirety herein. The present and other embodiments in the present specification may also be configured to provide heating to the replacement fluid at some point to permit the replacement fluid to evolve any dissolved gases which will settle out into the replacement fluid container 312 as the fluid circulates.

Figure 15:
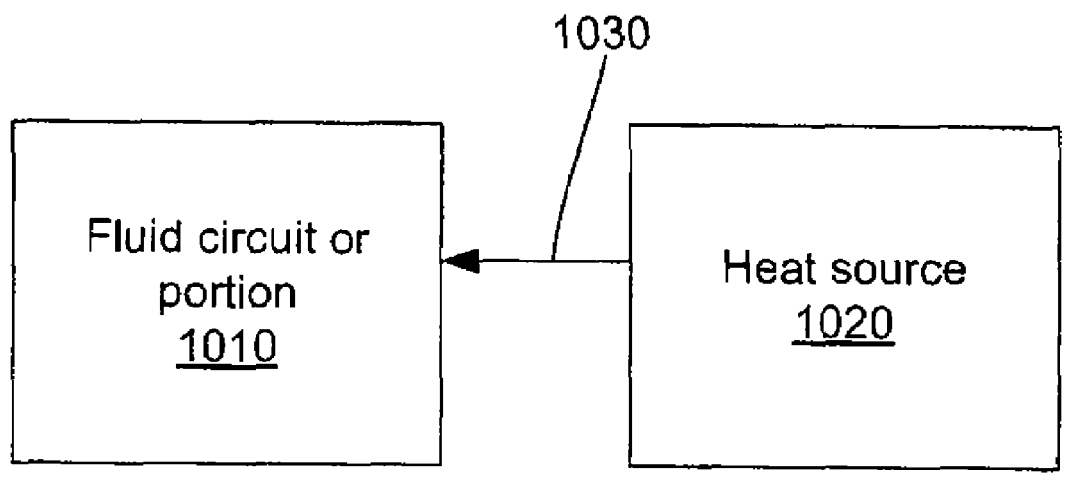
FIG. 15 illustrates the use of a heat source to supply heat to a portion of a fluid circuit according to various embodiments of the invention.
Figure 16:
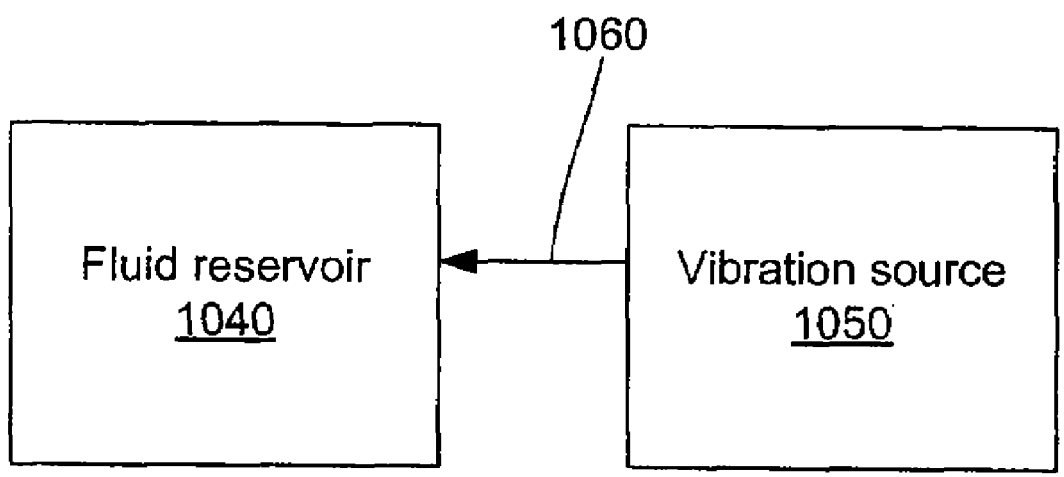
FIG. 16 illustrates the use of a vibration source to supply vibration to a fluid reservoir according to various embodiments of the invention.

As described, FIG. 15 illustrates the use of a heat source 1020 to supply heat (indicated at 1030) to a portion of a fluid circuit 1010 according to various embodiments of the invention. FIG. 16 illustrates the use of a vibration source 1050 to supply vibration (indicated at 1060) to a fluid reservoir 1040 according to various embodiments of the invention.

The flow in the fluid circuit waste side may be established after purging air from the replacement fluid side by continuous recirculation for a period of time. The flush of the waste side may be merely sufficient to push any air out of the waste side of the filter 324 and up to the balancing mechanism 310 and pump 350. A volume sufficient for that purpose would be optimal and the replacement fluid pump 316, the waste pump 334, the blood pump 322, and the ultrafiltrate pump 350 may be controlled by an automatic controller (not shown) accordingly.

Note that a venous branch 361 may be purged of air bubbles by appropriately regulating the relative speeds of the replacement fluid pump 316, the waste pump 334, the blood pump 322, and the ultrafiltrate pump 350. The pump speeds may be changed such that a substantial flow is established in the venous line 361 at a point in time after replacement fluid has been recirculated for a time. This may be done by changing the relative speeds from a state where the flow generally bypasses the venous line 361 to one where a substantial flow passes through it. For example, the latter may be obtained by halting the blood pump 322 and running the replacement fluid pump 316 in the forward direction (opposite the direction depicted in FIG. 11D) so that fluid flow toward the replacement fluid container 312 in line 311D from the venous line 361.

The following comments apply to all the above embodiments, not just that of FIG. 11D. Referring to FIGS. 11E and 11F, it is important in recirculating flow through the replacement fluid container 312 to ensure that bubbles have the opportunity to settle out. The accesses to the interior of a replacement fluid container 825A and 825B is preferably such that the opportunity for mixing of the incoming 827A, 827B and outgoing 829A, 829B flows is minimal. This prevents short-circuiting which would interfere with gas settling out of the flow, As indicated in FIG. 11E, this may be done by placing an incoming flow's 827A jet direction and location remote from the corresponding outgoing flow's 829A. Alternatively, or in addition, a barrier 831 may be used to separate the incoming 827A and outgoing 829A flows. An alternative is illustrated in FIG. 11F and discussed in U.S. application Ser. No. 10/393,185 filed Mar. 20, 2003 entitled "Dual Access Spike for Infusate Bags," which is hereby incorporated by reference as if fully set forth in its entirety herein. Referring to FIG. 11F, incoming 827B and outgoing 829B flows pass through a double-access spike that helps to prevent mixing of incoming 827B and outgoing 829B flows by ensuring the incoming flow 827B is propelled away from the zone of suction of the outgoing flow 829B.

In addition to causing gases to settle out in the replacement fluid container 312, imperfectly mixed electrolyte may also be better mixed by the process of pumping through the replacement fluid container 312. The uniformity may be monitored by means of a fluid quality sensor 317 which may be, for example, an inductive conductivity cell or wetted resistance sensor.

Figure 11G:
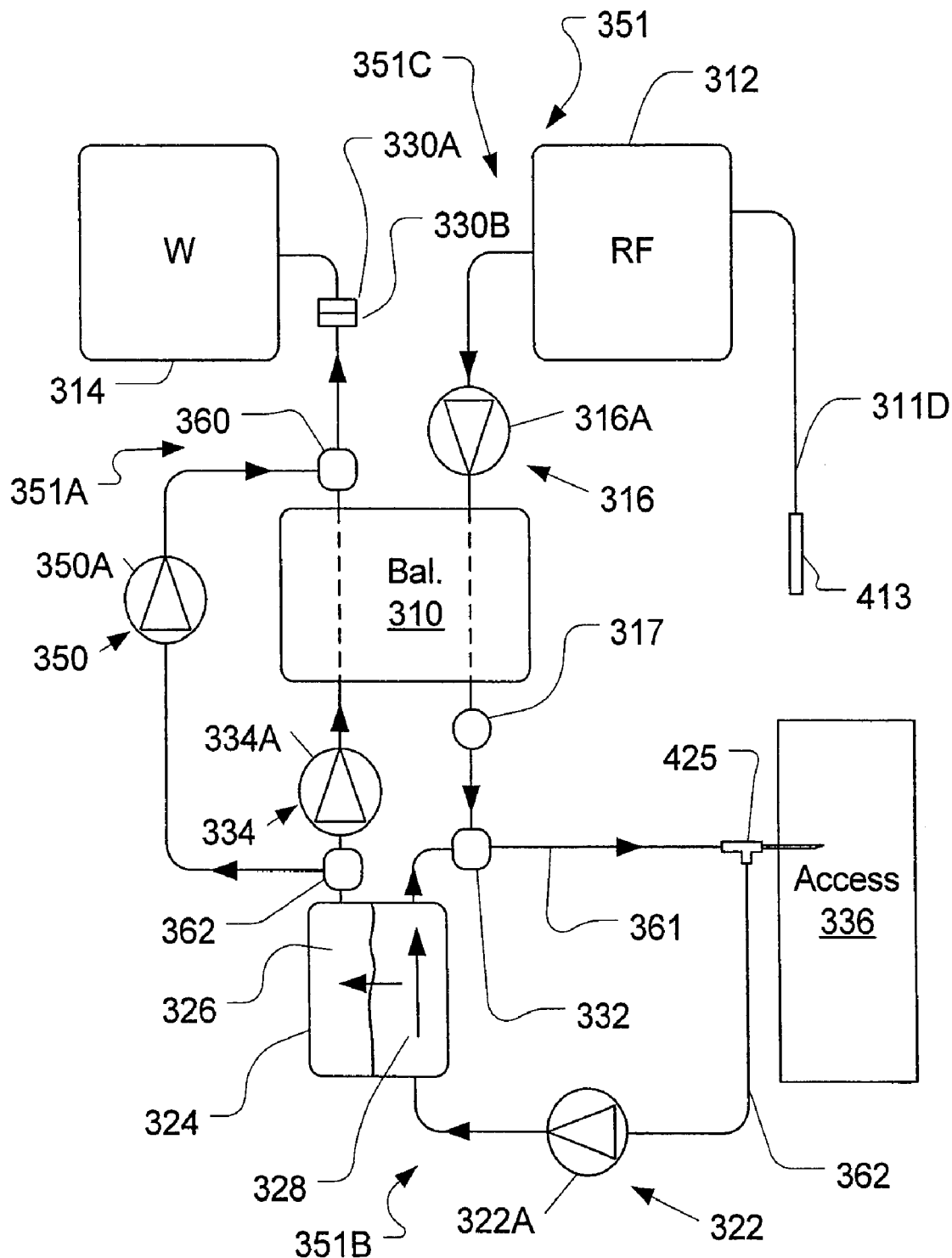
FIG. 11G illustrates the use of the embodiment of FIG. 11B with a fluid circuit during treatment.

Referring now to FIG. 11G, prior to treatment, the venous 361 and arterial 362 lines are clamped with typical tubing claims (not shown) and the double lumen access needle 425 removed from the connector 413. The connector automatically seals the line 311D as discussed above. The needle may then be inserted in a patient access 336. The replacement fluid pump 316, the waste pump 334, the blood pump 322, and the ultrafiltrate pump 350 may be activated and treatment begun. During treatment, blood circulates through the filter 324 urged by the blood pump 322 while waste is drawn off by the waste pump 334 and the ultrafiltrate pump 350. The balancing mechanism meters a flow of replacement fluid from the replacement fluid container 312, urged by the replacement fluid pump 316 and the resulting flow is added to the venous flow of blood returned via the double lumen access needle 425 into the patient.

Figure 12A:
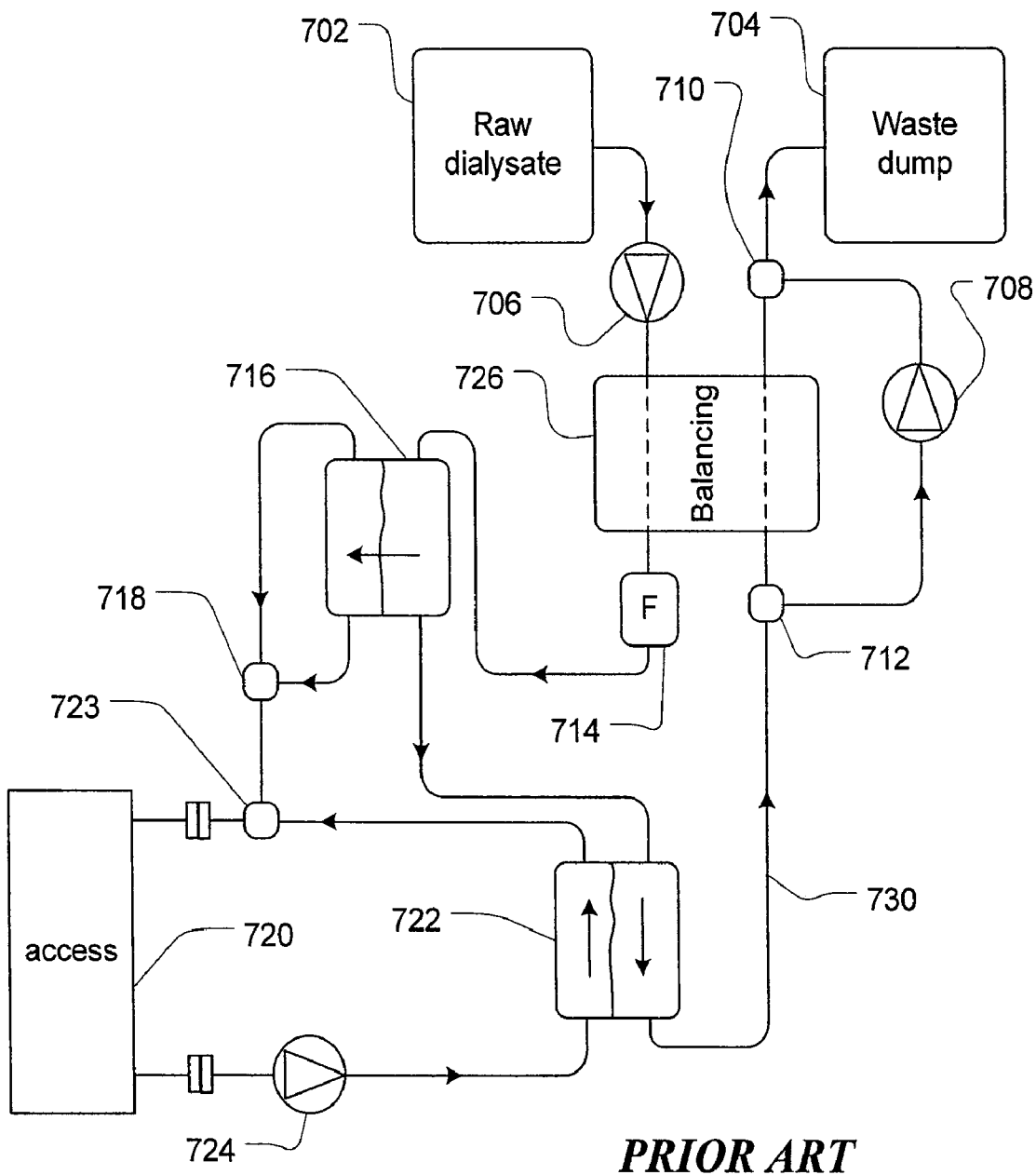
FIG. 12A illustrates a dialysis system embodiment of the prior art.

Referring to FIG. 12A, a dialysis system according to an embodiment of the prior art has a dialysate pump 706 which draws dialysis fluid from a raw dialysate source 702 and pumps it through a balancing mechanism 726, through a first stage purification filter 714, and into a second stage purification filter 716 where most of the flow bypasses the second stage filter 716 and flows into a dialyzer 722. Blood is circulated through the dialyzer 722 by a pump 724 and returned to the patient along with a small amount of fluid from the secondary filter 716 that passes through the junctions 718 and 723 to join with the flow of blood. The rate of flow of replacement fluid may be regulated using control valves or metering pumps (not shown) according methods known in the art. Most of the spent dialysate passes through the balancing mechanism 726, but part is bypassed by the utrafiltrate pump 708 such that a net fluid loss may be provided for maintaining the fluid balance of the patient according to known treatment methods.

Figure 12B:
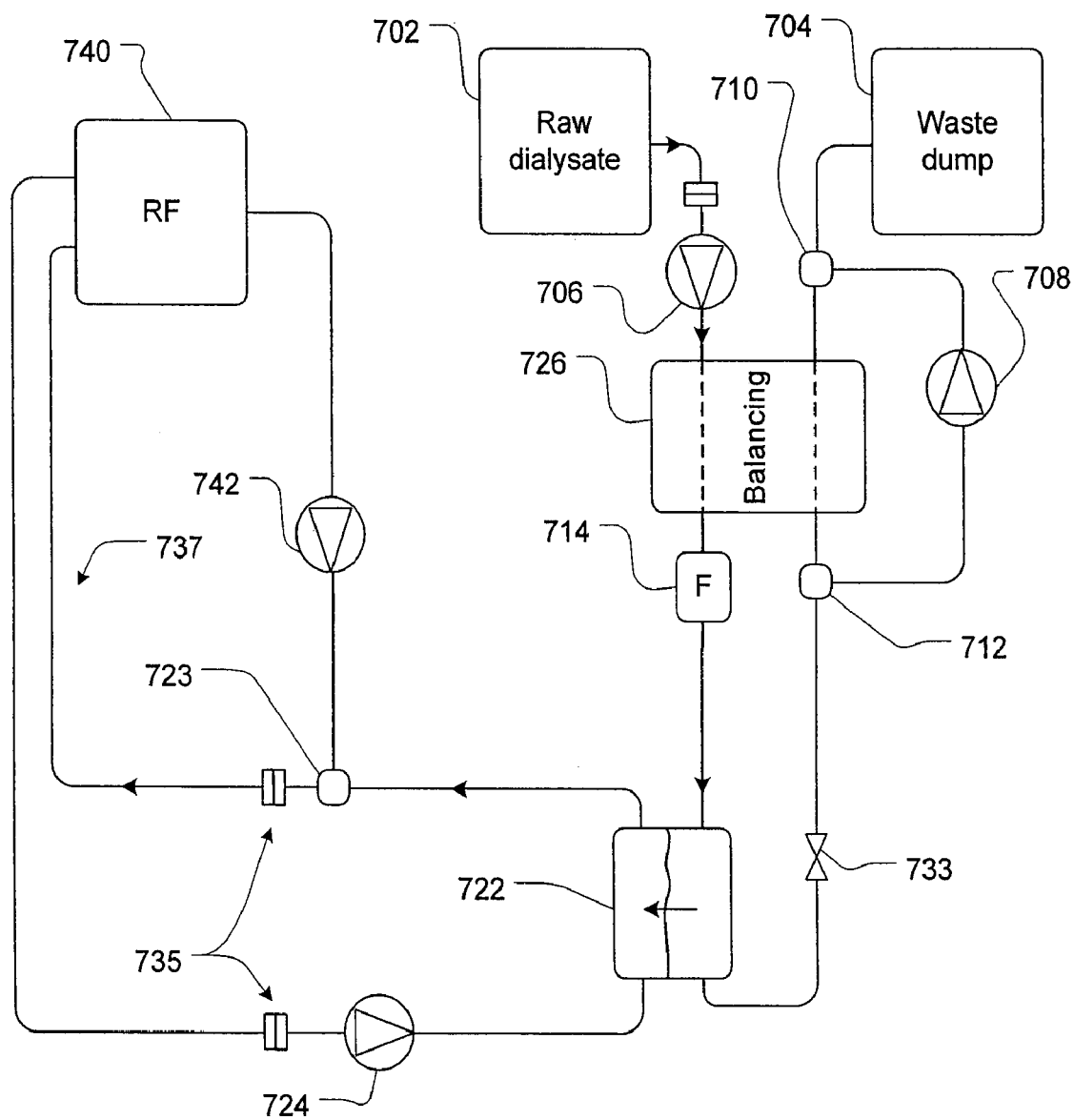
FIG. 12B illustrates a dialysis fluid circuit configured for replacement fluid preparation.
Figure 12C:
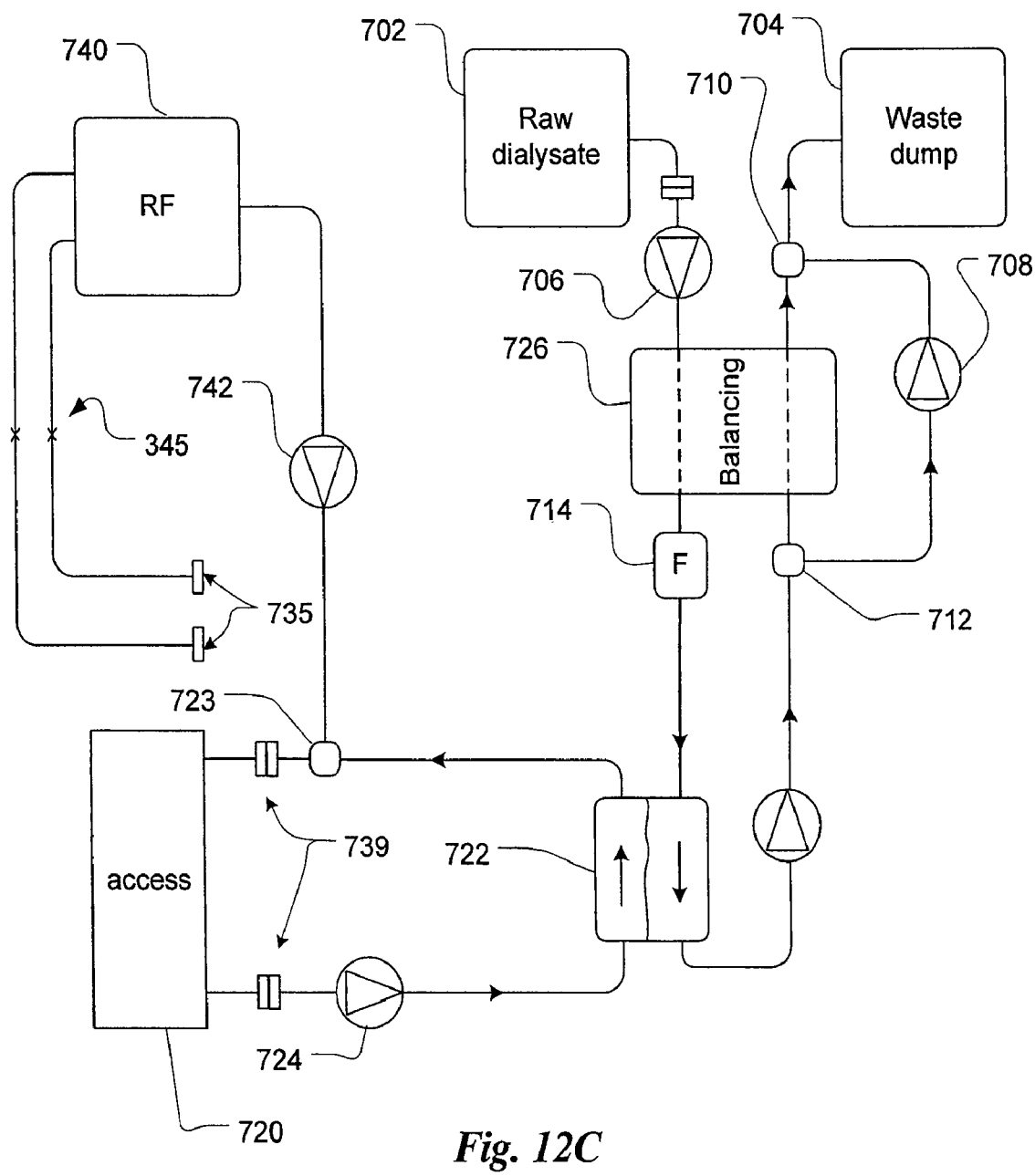
FIG. 12C illustrates a dialysis fluid circuit configured for treatment.

FIGS. 12B and 12C illustrate how the use of the inventive method and apparatus permits the second stage filter 716 to be eliminated. In FIG. 12B, replacement fluid is filtered by a first stage filter 714 and a dialyzer 722 providing first and second stage filtering as in the embodiment of FIG. 12A without the need for a separate filter 716. This is achieved by employing the dialyzer 722 as a purification filter to prepare a batch of replacement fluid prior to treatment. During a fluid preparation phase, as shown in FIG. 12B, raw dialysate is pumped from a source 702 by a pump 706 through a balancing mechanism 726, through a purification filter 714 while a control valve 733 is held closed. The filtered dialysate is thus filtered again as it passes through the membrane of the dialyzer 722, through a junction 723 and into the replacement fluid container 740 thereby filling it. After enough purified-filtered replacement fluid has been stored, the dialysis system is placed in treatment mode as illustrated in FIG. 12C.

Referring now also to FIG. 12C, the lines 737 are clamped as indicated at 345 and connectors 735 are disconnected and new connections 739 made to a patient access 720. As the dialysis treatment is initiated, replacement fluid is drawn from the replacement fluid container 740 and its flow metered by a replacement fluid pump 742. The rate of flow of replacement fluid may be determined by means of a flow measurement using known numerical, calibration, and control techniques that are well known and need not be delineated here. In other respects, the dialysis treatment proceeds as discussed with reference to FIG. 12A. As in previous embodiments, it should be clear from inspection that the fluid circuit may guard against touch contamination by providing a hermetically sealed system except for connections 739.

Figure 13:
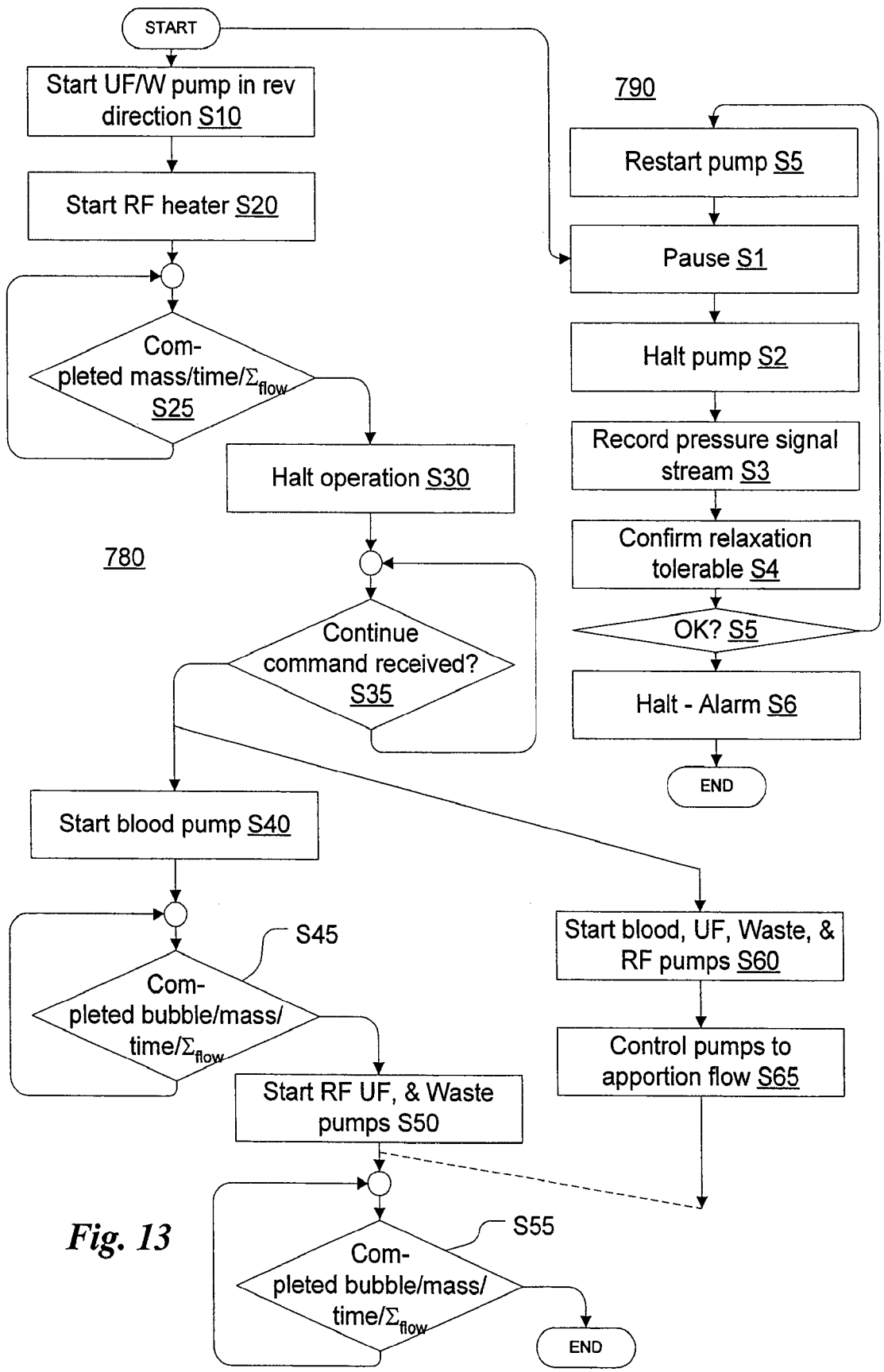
FIG. 13 is a flow chart illustrating an example of a control procedure for preparing replacement fluid and priming a fluid circuit of a hemofiltration system.

Referring now primarily to FIG. 13 but also to FIGS. 11C, 11D, and 11G, a representative control procedure for preparing replacement fluid and priming a fluid circuit begins with simultaneous execution of two parallel processes 780 and 790. The process 790 is a looping process that may continue throughout the execution of the 780 process as illustrated. Process 780 begins at step S10 with the initiation of the ultrafiltrate pump 350 in a reverse direction in the embodiments FIGS. 5 and 11C (or the waste pump in the embodiment of FIG. 8A). Immediately afterward at step S20, a replacement fluid heater (discussed in U.S. Patent Application Ser. No. 60/386,483 incorporated by reference above) may be activated to warm the replacement fluid captured in the replacement fluid container 312. Control flow loops through step S25 until some condition establishes that sufficient replacement fluid has been filtered. This condition may-be determined in various ways such as by weighing the filtered replacement fluid (filled RF container 312) or unfiltered replacement fluid (empty source container 314), by cumulating a measured mass flow rate of replacement fluid (by direct flow rate measurement or by pump shaft speed, for example), by cumulative pumping time, by detection of air in the line, etc.

Once the replacement fluid has been filtered, control branches to step S30 where a user may be alerted. Control loops through step S35 permitting a user to begin the priming process by generating a command at step S35 causing control to branch to step S40. Alternatively steps S30 and S35 may be omitted and priming may begin immediately with the execution of step S40. At step S40, the blood pump 322 may be started to begin pumping purified replacement fluid through the blood and replacement fluid circuits 351B and 311D. In the present embodiment, the priming flow in step S40 helps to carry any air away from the filter membrane and allow any bubbles to settle out of solution in the RF container 312. During this phase, a small amount of flow through the filter membrane may be permitted to ensure that bubbles are not later allowed into the primed blood and replacement fluid circuits. Control loops through step S45 for an interval sufficient to ensure that the-circuit is primed, the end of which may be determined by various means. For example, a bubble detector or fluid quality sensor 317 may be monitored until a signal from it falls below a threshold level. Alternatively, or in addition, the passage of a specified interval of time or the flow of a cumulative quantity of fluid may be detected. Control may also loop through step S45 waiting for the further condition of uniform fluid quality indicated by sensor 323. That is, an additional requirement of a constant fluid quality signal from that sensor may be required. This would be particularly advantageous if electrolytes were mixed with water at the treatment site.

After the above interval, at step S50, the waste, ultrafiltrate, and replacement fluid pumps 334, 350, and 316 may be started to purge and prime those lines. To purge the branch 361 in the embodiment of FIGS. 11C, 11D, and 11G, the replacement fluid pump 316 may be run at a much higher rate than the blood pump 322 during at least a portion of step S50. Various differences in the relative rates or sequencing of the waste, ultrafiltrate, and replacement fluid pumps 334, 350, and 316 may be provided to ensure the various lines are primed with relatively bubble-free replacement fluid. One such alternative is illustrated at steps S60 and S65 which may be substituted for steps S40, S45, and S50. In step S60, all the pumps are started and run, but their relative speeds are governed to ensure that air is purged as in the foregoing embodiments.

The continuously looping process 790 intermittently stops a pump, for example ultrafiltrate pump 350 while closing any relevant valves and stopping other pumps that may interfere, in order to gather data for testing filter membrane integrity. The process may be conducted during any of the steps of procedure 780 or all of them. The procedure may begin with a pause after which one or more pumps are halted together or in sequence such that a pressure relaxation trend may be recorded S3 using a pressure sensor (e.g., 331 in FIGS. 8A-8C) and a controller 331A. The relaxation curve may be compared to a template or to previously recorded curves to determine if the membrane is intact S4. If the test of S4 is passed, control passes to step S5 where the pumps are restarted (valves opened as required) to continue the current process. Otherwise in step S6 an alarm may be generated and other automatic actions taken as needed. Note that testing of backpressure may not require the stopping of pumps so the steps S2 and S5 may be omitted. IN such case, the continuous or intermittent pressure signal relative to the pump rate may be monitored as the pump (e.g., pump 334) operates.

Note that bubble traps may be used in the fluid circuit at various points and the RF container 312 may be provided with an air escape valve or membrane as discussed in system according to U.S. Pat. No. 6,572,641 entitled "Devices for warming fluid and methods of use" and filed Apr. 9, 2001, which is hereby incorporated by reference as if fully set forth in its entirety herein.

Figure 14A:
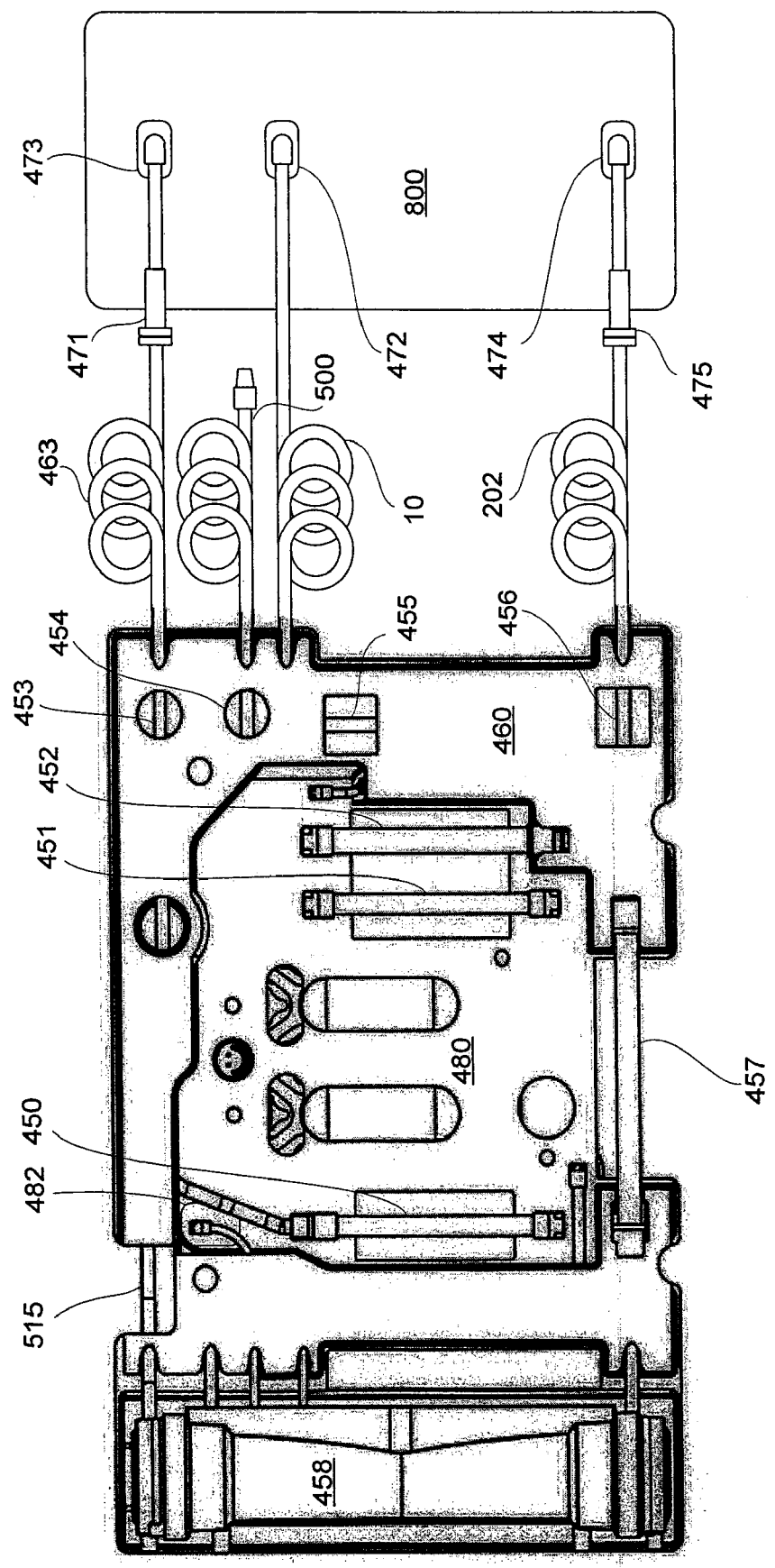
FIG. 14A is a diagram of a preferred embodiment of a fluid circuit set with a cartridge and filter in which a replacement fluid line is permanently attached to a replacement fluid reservoir.

Referring to FIG. 14A, a disposable fluid circuit with a filter 458 are partly supported by a cartridge 460 orienting for installation various components including balancing chambers 480, access points 515, 453, 454 456 455 and others for pressure, fluid quality, etc. measurement of blood, waste, dialysate and/or replacement fluid lines. Pumping regions 450, 451, 452, and 457 are also provided. The illustration is for a hemofiltration circuit but a similar structure would provide for hemodialysis or other blood treatments. Arterial 202 and venous 463 blood lines are preconnected by selective connectors 471 and 475 and permanent attachments 473 and 474 to replacement fluid container 800. A waste line 500 is capped and may be fitted with a connector for connecting to a waste bag or dump (not shown). The replacement fluid line 10 is permanently connected by attachment 472 to the replacement fluid container 800. All connections are such that the blood side of the filter is completely sealed and the only access required for preparation of purified replacement fluid is the waste line 500. The connectors 471 and 475 must be undone to connect to a patient access after sterilizing the replacement fluid which fills the container 800.

Figure 14B:
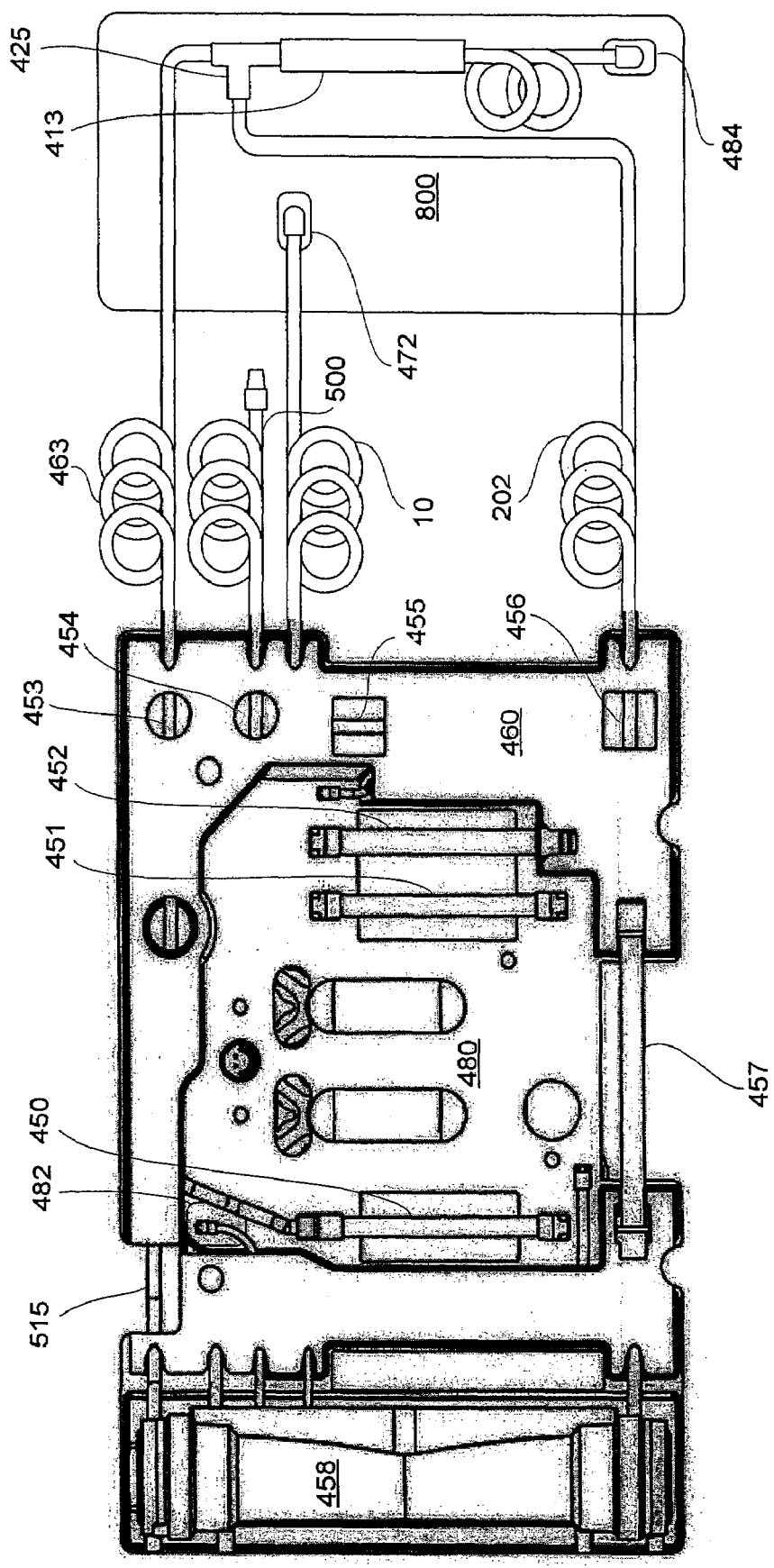
FIG. 14B is a diagram of a preferred embodiment of a fluid circuit set with a cartridge and filter in which a replacement fluid line is permanently attached to a replacement fluid reservoir and blood lines are permanently attached to a preconnected patient access needle.

Referring to FIG. 14B, in an alternative embodiment of a fluid circuit, similar to that of FIG. 14A, the replacement fluid line 10 is, again, permanently connected to the replacement fluid container 800. A common permanent connection 484 is provided to attach to the connector 413 which has, received therein, the dual lumen access needle 425. All connections are such that the blood side of the filter is completely sealed and the only access required for preparation of purified replacement fluid is the waste line 500. Only the connector 425/413 need be undone and in doing so, the connector 413 is automatically sealed as discussed above. In other respects, the embodiment of FIG. 14B is similar to that of FIG. 14A.

Although the foregoing invention has, for the purposes of clarity and understanding, been described in some detail by way of illustration and example, it will be obvious that certain changes and modifications may be practiced that will still fall within the scope of the appended claims. For example, the devices and methods of each embodiment can be combined with or used in any of the other embodiments. Although the fluid circuit examples described above included hemofiltration and hemodialysis circuits employing generic and volumetric balancing, it is possible to employ features of the embodiments with other kinds of balancing systems such as those described in U.S. Patent Application Ser. No. 60/440,176 filed Jan. 15, 2003 entitled "Waste balancing for extracorporeal blood treatment," hereby incorporated by reference as if fully set forth in its entirety herein. Also, further variations and details on preparation of replacement fluid are provided in the following application which is hereby incorporated by reference as if fully set forth in its entirety herein: U.S. Patent Application Ser. No. 60/438,567 filed Jan. 7, 2003 entitled "Preparation of replacement fluid by means of batch filtration prior to treatment."

What is claimed is:

1. A method for performing renal replacement therapy with a treatment device that employs a fluid circuit with liquid and blood fluid circuits separated by a membrane, the membrane having a pore size effective to block the passage of pyrogenic material, the method comprising: connecting a source of electrolytically-balanced fluid to the liquid fluid circuit; ensuring sterility of the electrolytically-balanced fluid by passing the same through the membrane to produce sterile fluid and storing the sterile fluid in a reservoir; warming and maintaining a temperature of the sterile fluid until a treatment time; recirculating the sterile fluid through the reservoir to permit gas to be purged from the sterile fluid by permitting gas to be floated out of the sterile fluid in the reservoir and prime a portion of the fluid circuit; priming a further portion of the fluid circuit.

2. A method as in claim 1, wherein the priming a further portion is executed after the recirculating.

3. A method as in claim 1, further comprising conveying blood from a patient through the blood fluid circuit during a treatment cycle and removing waste from the blood from the blood circuit through the membrane to the liquid fluid circuit.

4. A method as in claim 1, further comprising using the sterile fluid from reservoir in the process of performing a blood waste removing process on a patient.

5. A method as in claim 1, wherein the ensuring sterility includes ensuring a rate of endotoxins below a predetermined level by filtering with a membrane with a pore size effective to limit endotoxins.

6. A method as in claim 5, wherein the predetermined level is 3 EUs/ml. or less.

7. A method as in claim 1, further comprising vibrating the reservoir to aid in the removal of gas.

8. A method as in claim 1 wherein the passing the electrolytically-balanced fluid includes operating a blood pump in a first direction, the method further including conveying blood through the fluid circuit at the treatment time, the conveying blood including operating the blood pump in a second direction opposite the first direction.

9. A method for performing renal replacement therapy with a treatment device that employs a fluid circuit with liquid and blood fluid circuits separated by a membrane, the method comprising: connecting a source of electrolytically-balanced fluid to the liquid fluid circuit; passing the electrolytically-balanced fluid through the membrane and storing the resulting sterile fluid in a reservoir; warming the sterile fluid prior to a treatment time; and recirculating the sterile fluid through the reservoir to permit gas to be purged from the sterile fluid and prime at least a portion of the fluid by permitting gas to be floated out of the sterile fluid in the reservoir circuit.

10. A method as in claim 9, further comprising priming a further portion of the fluid circuit after recirculating the sterile fluid through the reservoir.

11. A method as in claim 9, further comprising conveying blood from a patient through the blood fluid circuit during a treatment cycle and removing waste from the blood from the blood circuit through the membrane to the liquid fluid circuit.

12. A method as in claim 9, further comprising using the sterile fluid from reservoir in the process of performing a blood waste removing process on a patient.

13. A method as in claim 9, wherein the passing the electrolytically-balanced fluid through the membrane includes providing a rate of endotoxins below a predetermined level by filtering with a membrane with a pore size effective to limit endotoxins.

14. A method as in claim 13, wherein the predetermined level is 3 EUs/ml. or less.

15. A method as in claim 9, further comprising vibrating the reservoir to aid in the removal of gas.

16. A method as in claim 9 wherein the passing the electrolytically-balanced fluid includes operating a blood pump in a first direction, the method further including conveying blood through the fluid circuit at the treatment time, the conveying blood including operating the blood pump in a second direction opposite the first direction.

* * * * *